(12) United States Patent
Caligiuri et al.

(10) Patent No.: US 6,747,128 B2
(45) Date of Patent: *Jun. 8, 2004

(54) COMPONENTS OF UBIQUITIN LIGASE COMPLEXES, AND USES RELATED THERETO

(75) Inventors: Maureen Caligiuri, Reading, MA (US); Mark Rolfe, Newton, MA (US)

(73) Assignee: GPC Biotech, Inc., Waltham, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/915,048

(22) Filed: Aug. 20, 1997

(65) Prior Publication Data

US 2002/0025569 A1 Feb. 28, 2002

(51) Int. Cl.[7] ............................ C07K 14/00; C12N 9/00
(52) U.S. Cl. ............... 530/350; 435/252.3; 435/254.11; 435/320.1; 435/219; 435/183; 435/325; 536/23.1; 536/23.2; 536/23.5; 530/350
(58) Field of Search ............................... 435/183, 252.3, 435/254.11, 325, 320.1; 536/23.1, 23.2, 23.5; 530/350

(56) References Cited

U.S. PATENT DOCUMENTS

| 5,384,255 A | 1/1995 | Ciechanover et al. ....... 435/193 |
| 5,532,348 A | 7/1996 | Huibregtse et al. ......... 536/23.5 |

FOREIGN PATENT DOCUMENTS

| WO | WO 89/09829 | 10/1989 |
| WO | WO 89/12678 | 12/1989 |
| WO | WO 91/17245 | 11/1991 |
| WO | WO 92/20804 | 11/1992 |
| WO | WO 93/09235 | 5/1993 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492–495.*
Marra et al. (1996) The Washington University–HHMI Mouse EST Project. Genbank ACCESSION No. AA171151, Dec. 1996.*
Sigma Catalog (1993) Catalog No. A2383, Jan. 1993.*
Auffray et al. (1995) C. R. Acad. Sci. III, Sci. Vie 318 (2): 263–272, Mar. 1995.*
Adams et al. (1993) "Rapid cDNA sequencing (expressed sequence tags) from a directionally cloned human infant brain cDNA library", Nature Genetics 4:373–380.
Band et al. (1991) "Loss of p53 Protein in Human Papillomarvirus Type 16 E6–Immortalized Human Mammary Epithelial Cells", J. Virol., 65(12):6671–6676–87.
Berleth et al. (1992) "Inhibition of Ubiquitin–Protein Ligase (E3) by Mono–and Bifunctional Phenylarsenoxides", J.Biol. Chem. 267(23):16403–16411.
Bissonnette et al. (1992) "Apoptotic cell death induced by c–myc is inhibited by bcl–2", Nature 359:552–554.
Chen et al. (1993) "Multiple Ubiquitin–Conjugating Enzymes Participate in the In Vivo Degradation of the Yeast MATα2 Repressor", Cell 74:357–369. (1993).
Ciechanover et al. (1991) "Degradation of Nuclear Oncoproteins by the Ubiquitin System in Vitro", Proc. Natl. Acad. Sci. USA 88:139–143.
Cook et al. (1993) "Tertiary Structures of Ubiquitin–Conjugating Enzymes Are Highly Conserved: Crystal Structure of Yeast Ubc4", Biochemistry 32(50):13809–13817.
Cook et al. (1992) "Structure of a Diubiquitin Conjugate and a Model for Interaction with Ubiquitin Conjugating Enzyme (E2)", J. Biol. Chem. 267(23):16467–16471.
Crook et al. (1991) "Degradation of p53 Can Be Targeted by HPV E6 Sequences Distinct from Those Required for p53 Binding and Trans–Activation", Cell 67:547–556.
Dohmen et al. (1991) "The N–end rule is mediated by the UBC2(RAD6) ubiquitin–conjugating enzyme", Proc. Natl. Acad. Sci. 88:7351–7355.
Ellison et al. (1991) "Epitope–tagged Ubiquitin", J. Biol Chem 266(31):21150–21157.
Evan et al. (1992) "Induction of Apoptosis in Fibroblasts by c–myc Protein", Cell 69:119–128.
Girod et al. (1993) "Homologs of the essential ubiquitin–conjugating enzymes UBC1, 4, and 5 in yeast are encoded by a multigene family in Arabidopsis thaliana", The Plant Journal 3(4):545–552.
Glotzer et al. (1991) "Cyclin is degraded by the ubiquitin pathway", Nature 349:132–138.

(List continued on next page.)

Primary Examiner—Richard Hutson
(74) Attorney, Agent, or Firm—Ropes & Gray LLP

(57) ABSTRACT

The present invention relates to the isolation of a new class of ubiquitin ligases involved in protein degradation in vertebrate organisms, such as protein degradation of cell cycle regulatory proteins. Accordingly, the invention provides nucleic acids and the proteins encoded by said nucleic acids which play a role in the ubiquitinylation and subsequent degradation of substrate proteins and in regulating cell proliferation, cell differentiation, and cell survival. The invention also provides methods for modulating protein degradation, cell proliferation, cell differentiation and/or cell survival by modulating protein ubiquitination; assays for identifying compounds which modulate protein degradation, cell proliferation, differentiation and/or cell survival; methods for treating disorders associated with aberrant protein degradation, cell proliferation, cell differentiation, and/or cell survival; and diagnostic and prognostic assays for determining whether a subject is at risk of developing a disorder associated with an aberrant protein degradation, cell proliferation, cell differentiation, and/or survival.

18 Claims, 2 Drawing Sheets

OTHER PUBLICATIONS

Hartwell et al. (1992) "Defects in a Cell Cycle Checkpoint May Be Responsible for the Genomic Instability of Cancer Cells", *Cell 71*:543–546.

Hershko et al. (1993) "Components of Ubiquitin–Protein Ligase System", *J. Biol. Chem. 258*(13):8206–8214.

Hochstrasser et al. (1990) "In Vivo Degradation of a Transcriptional Regulator: The Yeast α2 Repressor", *Cell 61*:697–708.

Hochstrasser et al. (1991) "The Short–lived MAT α2 Transcriptional Regulator is Ubiquitinated in Vivo", *Proc. Natl. Acad. Sci. USA 88*:4606–4610.

Hoefer et al. (1991) "Purification and partial characterization of ubiquitin–activating enzyme from *Saccharomyces cerevisiae*", *FEBS Letters 289*(1):54–58.

Holloway et al. (1993) "Anaphase is Initiated by Proteolysis Rather Than by the Inactivation of Maturation–Promoting Factor", *Cell 73*:1393–1402.

Huibregtse et al. (1993) "Cloning and Expression of the cDNA for E6–AP, a Protein That Mediates the Interaction of the Human Papillomavirus E6 Oncoprotein with p53", *Mol Cell Biol 13*(2):775–784.

Huibregtse et al. (1993) "Localization of the E6–AP Regions That Direct Human Papillomavirus E6 Binding, Association with p53, and Ubiquitination of Associated Proteins", *Mol Cell Biol 13*(8):4918–4927.

Huibregtse et al. (1995) "A Family of Proteins Structurally and Functionally Related to the E6–AP Ubiquitin–protein Ligase", *Proc. Natl. Acad. Sci. USA 92*:2563–2567.

Huibregtse et al. (1991) "A cellular protein mediates association of p53 with the E6 oncoprotein of human papillomavirus types 16 or 18", *EMBO J. 10*(13):4129–4135.

Hupp et al. (1992) "Regulation of the Specific DNA Binding Function of p53", *Cell 71*:875–886.

Jacobs et al. (1993) "Rapid Assessment of Drug Susceptibilities of *Mycobacterium tuberculosis* by Means of Luciferase Reporter Phages", *Science 260*:819–822.

Jentsch (1992) "The Ubiquitin–conjugation System", *Ann Rev Genet 26*:179–207.

Klemperer et al. (1989) "A Novel, Arsenite–Sensitive E2 of the Ubiquitin Pathway: Purification and Properties", *Biochemistry 28*:6035–6041.

Koken et al. (1991) "Structural and Functional Conservation of Two Human Homologs of the Yeast DNA Repair Gene RAD6", *Proc. Natl. Acad. Sci. 88*8865–8869.

Kumar et al. (1992) "Identification of a set of genes with developmentally–down–regulated expression in the mouse brain", Biochem. Biophys. Res. Comm. 185: 1155–1161.

Milner et al. (1990) "p53 Is Associated with $p34^{cdc2}$ In Transformed Cells", *EMBO J. 9*(9):2885–2889.

Münger et al. (1989) "The E6 and E7 Genes of the Human Papillomavirus Type 16 Together Are Necessary and Sufficient for Transformation of Primary Human Keratinocytes", *J. Virol. 63*(10):4417–4421.

Nefsky et al. (1996) "Pub1 acts as an E6–AP–like protein ubiquitin ligase in the degradation of cdc25", *EMBO J. 15*(16):1301–1312.

Nepveu et al. (1987) "Alternative modes of *c–myc* regulation in growth factor–stimulated and differentiating cells", *Oncogene 1*:243–250.

Rechsteiner et al. (1991) "Natural Substrates of the Ubiquitin Proteolytic Pathway", *Cell 66*:615–618.

Schärer et al. (1992) "Mammalian p53 can function as a transcription factor in yeast", *Nucleic Acids Research 20*(7):1539–1545.

Scheffner et al. (1992) "Interaction of the Human Papillomavirus Type 16 E6 Oncoprotein with Wild–Type and Mutant Human p53 Proteins", *J. Virol. 66*(8):5100–5105.

Scheffner et al. (1990) "The E6 Oncoprotein Encoded by Human Papillomavirus Types 16 and 18 Promotes the Degradation of p53", *Cell 63*:1129–1136.

Scheffner et al. (1992) "Targeted degradation of the retinoblastoma protein by human papillomavirus E7–E6 fusion proteins", *EMBO J. 11*(7):2425–2431.

Scheffner et al. (1993) "The HPV–16 E6 and E6–AP Complex Functions as a Ubiquitin–Protein Ligase in the Ubiquitination of p53", *Cell 75*:495–505.

Seufert and Jentsch (1990) "Ubiquitin–conjugating enzymes UBC4 and UBC5 mediate selective degradation of short–lived and abnormal proteins", *EMBO J. 9*(2):543–550.

Treier et al. (1992) "*Drosophila UbcD1* encodes a highly conserved ubiquitin–conjugating enzyme involved in selective protein degradation", *EMBO J. 11*(1):367–372.

Tyers et al. (1992) "The Cin3–Cdc28 kinase complex of *S. cerevisiae* is regulated by proteolysis and phosphorylation", *EMBO J. 11*(5):1773–1784.

Watanabe et al. (1989) "Human Papillomavirus Type 16 Transformation of Primary Human Embryonic Fibroblasts Requires Expression of Open Reading Frames E6 and E7", *J. Virol. 63*(2):965–969.

Wilkinson (1990) "Detection and Inhibition of Ubiquitin–Dependent Proteolysis", *Methods in Enzymology 185*:387–397.

Zhen et al. (1993) "The *ubc*–2 Gene of *Caenorhabditis elegans* Encodes a Ubiquitin–Conjugating Enzyme Involved in Selective Protein Degradation", *Mol Cell Biol 13*(3):1371–1377.

* cited by examiner

Figure 1

MDALEDYVWP RATSELILLP VTGLECVGDR LLAGEGPDVL VYSLDFGGHL RMIKRVQNLL

GHYLIHGFRV RPEPNGDLDL EAMVAVFGSK GLRVVKISWG QGHFWELWRS GLWNMSDWIW

DARWLEGNIA LALGHNSVVL YDPVVGCILQ EVPCTDRCTL SSACLIGDAW KELTIVAGAV

SNQLLVWYPA TALADNKPVA PDRRISGHVG IIFSMSYLES KGLLATASED RSVRIWKVGD

<u>LRVPGGRVQN IGHCFGHSAR VWQVKLLENY LISAGEDCVC LVWSHEGEIL</u> QAFRGHQGRG
|----------------F- box------------------|

IRAIAAHERQ AWVITGGDDS GIRLWHLVGR GYRGLGVSAL CFKSRSRPGT LKAVTLAGSW

RLLAVTDTGA LYLYDVEVKC WEQLLEDKHF QSYCLLEAAF GPEGFGLCAM ANGEGRVKVV

PINTPTAAVD QTLFPGKVHS LSWALRGYEE LLLLASGPGG VVACLEISAA PSGKAIFVKE

RCRYLLPPSK QRWHTCSAFL PPGDFLVCGD RRGSVLLFPS RPGLLKDPGV GGKARAGAGA

FVVGSGSSGG GNAFTGLGPV STLPSLHGKQ GVTSVTCHGG YVYTTCRDGA YYQLFVRDGQ

LQPVLRQKSC RGMNWLAGLR IVPDGSMVIL GFHANEFVVW N<u>PRSHEKLHI VNCGGGHRSW</u>

<u>AFSDTEAAMA FAYLKDGDVM LYRALGGCTR PHVILREGLH GREITCVKRV GTITLGPEYG</u>

<u>VPSFMQPDDL EPGSEGPDLT DIVITCSEDT TVCVLALPTT TGSAHALTAV CNHISSVRAV</u>

<u>AVWGIGTPGG PQDPOPGLTA HVVSAGGRAE MHCFSIMVTP DPSTPSRLAC HVMHLSSHRL</u>
                                  *
<u>DEYWDRORNR HRMVKVDPET RYMSLAVCEL DQPGLGPLVA AACSDGAVRL FLLQDSGRIL</u>

<u>QLLAETFHHK RCVLKVHSFT HEAPNQRRRL LLCSAATDGS LAFWDLTTML DHDSTVLEPP</u>

<u>VDPGLPYRLG TPSLTLQAHS CGINSLHTLP TREGHHLVAC GSEDGSLHVF VLAVEMLQLE</u>

<u>EAVGEAGLVP QLRVLEEYSV PCAHAAHVTG LKILSPSIMV SASIDQRLTF WRLGHGEPTF</u>

MNSTVFHVPD VADMDCWPVS PEFGHRCALG GQGLEVYNWY D

Figure 2

COMPONENTS OF UBIQUITIN LIGASE COMPLEXES, AND USES RELATED THERETO

BACKGROUND OF THE INVENTION

The ubiquitin-mediated proteolysis system is the major pathway for the selective, controlled degradation of intracellular proteins in eukaryotic cells. Ubiquitin modification of a variety of protein targets within the cell appears to be important in a number of basic cellular functions such as regulation of gene expression, regulation of the cell-cycle, modification of cell surface receptors, biogenesis of ribosomes, and DNA repair. One major function of the ubiquitin-mediated system is to control the half-lives of cellular proteins. The half-life of different proteins can range from a few minutes to several days, and can vary considerably depending on the cell-type, nutritional and environmental conditions, as well as the stage of the cell-cycle.

Targeted proteins undergoing selective degradation, presumably through the actions of a ubiquitin-dependent proteosome, are covalently tagged with ubiquitin through the formation of an isopeptide bond between the C-terminal glycyl residue of ubiquitin and a specific lysyl residue in the substrate protein. This process is catalyzed by a ubiquitin-activating enzyme (E1) and a ubiquitin-conjugating enzyme (E2), and in some instances may also require auxiliary substrate recognition proteins (E3s). Following the linkage of the first ubiquitin chain, additional molecules of ubiquitin may be attached to lysine side chains of the previously conjugated moiety to form branched multi-ubiquitin chains.

The conjugation of ubiquitin to protein substrates is a multi-step process. Ubiquitin is a small, highly curved protein which must be activated before it is transferred to a substrate protein. Accordingly, in an initial ATP requiring step, a thioester is formed between the C-terminus of ubiquitin and an internal cysteine residue of a ubiquitin activating enzyme, E1. Activated ubiquitin is then transesterified to a specific cysteine on one of several E2 enzymes. Finally, these E2 enzymes transfer ubiquitin to a lysine residue of a protein substrate. Substrates are recognized either directly by ubiquitin-conjugated enzymes or by associated substrate recognition proteins, the E3 proteins, also known as ubiquitin ligases. A major cellular mechanism by which proteins are degraded in eukaryotic cells is by ubiquitinylation of the protein, thereby targeting the protein for degradation by the 26S proteasome (Hochstrasser (1995) *Curr. Opin. Cell Biol.* 7:215). Ubiquitin is a small, highly conserved protein, which must be activated before it is transferred to a substrate protein. Activation of ubiquitin occurs through formation of a thioester bond between the COOH terminus of the ubiquitin molecule and a ubiquitin-activating enzyme, E1. Ubiquitin is then transesterified to one member of a family of a ubiquitin conjugating enzymes, E2 enzymes. Ubiquitin is then transferred, either directly or indirectly, to a lysine residue of a substrate protein. Transfer to the substrate protein may require the assistance of a ubiquitin ligase also termed E3 enzyme or complex. An E3 is generally required for the formation of multiubiquitin chains on the substrate, a step that facilitates efficient recognition of the substrate by the proteosome. It has been suggested that E3 is the primary source of substrate specificity in the ubiquitination cascade, as some E3s have been shown to directly bind substrates (Hershko et al. (1986) *J. Biol. Chem.* 261:11992; Bartel et al. (1990) *EMBO J.* 9:3179). Furthermore, in some situations, a ubiquitin molecule is first transferred from an ubiquitin conjugating enzyme to an E3 enzyme or complex, prior to being transferred to the substrate protein (Willems et al., supra).

Ubiquitination of proteins and subsequent protein degradation plays an important role in various steps of the cell cycle and is thus crucial in the regulation of cell proliferation and differentiation. Briefly, cell-cycle events are thought to be regulated by a series of interdependent biochemical steps. In eukaryotic cells mitosis does not normally take place until the G1, S and G2 phases of the cell-cycle are completed. In all eukaryotic cells examined to date, the cell cycle appears to be regulated by the sequential activation of a series of the CDK's or Cyclin Dependent Kinases (reviewed in Morgan, (1995) *Nature* 374:131–134; King et al., (1994) *Cell* 79:563–571; Norbury and Nurse, (1992) *Annu. Rev. Biochem.* 61:441–470). Yeast cells contain a single CDK known as cdc2 in *S. pombe* (Beach et al., (1982) *Nature* 300:706–709; Booher and Beach, (1986) *Gene* 31:129–134; Hindley and Phear, (1984) *Gene* 21:129–134; Nurse and Bissett, (1981) *Nature* 292:558–560; Simanis and Nurse, (1986) *Cell* 45:261–268; and for review see Forsburg and Nurse, (1991b) *Annu. Rev. Cell Biol.* 7:227–256) and cdc28 in *S. cerevisiae*. Drosophila and vertebrates have several CDKs, including CDK1, CDK2, CDK4, and CDK6 (Elledge S. J. (1996) *Science* 274:1664).

The activity of the CDKs is controlled at least in part by the association of the CDKs with various cyclins during progression through the cell cycle. Cyclins also contribute to substrate specificity The CDK-cyclin complex is both positively and negatively regulated by several mechanisms including phosphorylation, binding to inhibitors (CKIs) and other proteins such as Suc1 (Cks1) that might modify their specificity or accessibility to regulators, and protein degradation by the ubiquitin conjugation pathway (Patra et al. (1996) *Genes Dev.* 10:1503).

In addition to their role in activating mitosis, the cyclin-CDKs are required to stimulate the initiation of DNA replication. In yeast, the activity of cyclin-CDKs is blocked specifically by the inhibitor Sic1, which is present in cells from late mitosis until shortly after START. Thus, degradation of Sic1 is necessary for DNA replication. In yeast, it has been shown that degradation of this protein is mediated by the ubiquitin conjugating enzyme (E2) Cdc34 and also requires cdc4 and cdc53 and a Skp1 protein. These proteins are also involved in degradation of other cell cycle regulatory proteins in yeast, including the G1 cyclins, which are required for executing the START of the cell cycle (King et al. (1996) *Science* 274:1653; Willens et al. (1996) *Cell* 86:453; Bai et al. (1996) *Cell* 86: 263; and Mathias et al (1996) *Mol. Cell. Biol.* 16:6634).

In particular, molecular cloning of cdc34, a gene required for the G1-S transition in budding yeast, revealed that a ubiquitin conjugation step was required just before the initiation of DNA replication. cdc34 encodes a ubiquitin conjugating enzyme that participates in the destruction of multiple proteins, including the G1 cyclins CLN2 and CLN3, as well as proteins not directly related to cell cycle control. However, accumulation of these substrates does not account for the cell cycle arrest of cdc34$^{ts}$ mutants. The nature of the crucial target of cdc34 at the G1-S transition was first implied by genetic studies. A strain deficient in all S-phase and mitotic cyclins recapitulated the cdc34$^{ts}$ mutant phenotype, suggesting that the cdc34 pathway might be required for generating S-phase CDK activity. Extracts made from cdc34$^{ts}$ mutants inhibit S-phase CDKs, implying that cdc34 may be required for the degradation of a CDK inhibitor. A candidate for this activity was SIC1, a tightbinding S-phase CDK inhibitor (Mendenhall (1993) *Science* 259:216; Nugroho et al. (1994) *Mol Cell. Biol.* 14:3320). SIC1 is normally degraded as wild-type cells enter S phase, but accumulates in cdc34$^{ts}$ mutants. SIC1 appears to be the crucial substrate blocking progression from G1 to S phase in cdc34$^{ts}$ mutants, because cdc34$^{ts}$ sic1Δ double mutants initiate DNA replication at the nonpermissive temperature (Schwob et al. (1994) *Cell* 79:233). As predicted by these findings, expression of a non-degradable form of SIC1 in wild-type strains blocks cell division at the G1-S transition (King et al. (1996) *Science* 274: 1652). Ubiquitin-dependent proteolysis of a CDK inhibitor is therefore a crucial mechanism by which the onset of S phase is controlled.

Besides cdc34, three other genes are required for the G1-S transition in budding yeast: cdc4, cdc53, and SKP1 (King et al. supra). Cells with temperature-sensitive mutations in any of these genes exhibit phenotypes similar to that of cdc34$^{ts}$ mutants, and in each case deletion of SIC1 enables these mutants to replicate their DNA. Both cdc53 and SKP1 are members of conserved, multigene families, but there is little information about their biochemical functions. cdc4 contains two recognizable sequence motifs that are found in many unrelated proteins: an F box, which serves as an interaction domain for SKP1 (Bai et al. (1996) *Cell* 86:263), and eight WD-40 repeats (Neer et al. (1994) *Nature* 371:297), which may serve as a platform for protein-protein interaction (Sondek et al. (1996) *Nature* 379:369). Insect cell lysates expressing cdc53, cdc4, and SKP1 (and supplemented with cdc34, ubiquitin, and E1) can sustain ubiquitination of SIC1, suggesting that one of these components functions as an E3 (King et al. supra).

SUMMARY OF THE INVENTION

One aspect of the present invention relates to a new class of ubiquitin ligases, the "SIP ligases" for SKP Interacting Proteins. The mammalian homolog of cdc4 is an archetype for the ligase family. The present invention provides isolated and/or recombinant forms of the *SIP ligase,* and portions thereof. For instance, there is provided isolated and/or recombinant cdc4 polypeptides having an amino acid sequence identical or homologous (e.g. at least 65, 75, 85 or 95%) to the amino acid sequence designated by SEQ ID NO: 2 or 4. The cdc4 polypeptide can have an amino acid sequence encoded by a nucleic acid which hybridizes under stringent conditions to the nucleotide sequence set forth in SEQ ID NO: 1 or 3. The SIP polypeptides of the present invention are preferably encoded by a vertebrate gene, more preferably a mammalian gene, and even more preferably a human gene.

In preferred embodiments, the SIP polypeptides can be components of a ubiquitin ligase complex, e.g., which catalyze ubiquitinylation of a cell cycle regulatory protein such as p27$^{kip1}$. For instance, the polypeptide is capable of interacting with at least one other protein selected from the group consisting of a component of a ubiquitin ligase, a skp1 protein, a ubiquitin conjugating enzyme, a cullins, and a p27 protein or a (G1 phase) cyclin.

Still another aspect of the present invention provides nucleic acids which encode the subject SIP polypeptides, e.g., which nucleic acid hybridize under stringent conditions to a nucleic acid probe having a nucleotide sequence represented by at least 20, 40, 60, 80 or 100 consecutive nucleotides of SEQ ID NO: 1 or 3, or a sequence complementary thereto. In a preferred embodiment, the nucleic acid comprises the nucleotide sequence set forth in SEQ ID NO: 1 or 3.

The subject nucleic acid can be used to generate expression constructs, such as by placing a transcriptional regulatory sequence in operable linkage with the SIP coding sequence. Accordingly, expression vectors encoding the subject polypeptides can be generated using expression vectors capable of replicating in at least one of a prokaryotic cell and a eukaryotic cell.

Thus, another aspect of the present invention pertains to a host cell transfected with such an expression vector, e.g., expressing recombinant SIP polypeptides, as well as methods of producing a recombinant SIP polypeptide by culturing the instant cell to express the recombinant polypeptide.

The present invention also relates to transgenic animals having cells which harbor a transgene encoding a recombinant SIP polypeptide, or in which the endogenous gene has been inactivated, e.g., by homologous recombination.

Still another embodiment of the present invention relates to isolated nucleic acid which selectively hybridizes under high stringency conditions to at least ten nucleotides of a nucleic acid sequence represented by one of SEQ ID NO: 1 or SEQ ID NO: 3, or complementary sequences thereof, which nucleic acid can specifically detect or amplify a nucleic acid sequence of an vertebrate cdc4. Such nucleic acid can be used, e.g., to generate the expression constructs described above, as well as various assays for detecting SIP genes or transcripts, or for antisense therapy. In a preferred embodiment, the nucleic acid is labeled.

Yet another aspect of the present invention provides reconstituted protein mixtures including a SIP ligase, along with a substrate protein, such as a p27$^{kip1}$ polypeptide or other CKI protein. The mixture may further include ubiquitin, an E1 enzyme, an E2 enzyme and/or a cullins protein. As appropriate, the E1, E2 or SIP enzymes used to charge the mixture can be provided as transiently ubiquitinated intermediates.

Still another aspect of the present invention pertains to an assay for identifying an inhibitor of SIP-mediated ubiquitination. In a preferred embodiment, the assay comprises a ubiquitin-conjugating system including the substrate polypeptide, ubiquitin and a SIP ligase, under conditions which promote ubiquitination of the substrate polypeptide by the SIP ligase. The ubiquitin-conjugating system is contacted with a candidate agent, and the level of ubiquitination of the substrate polypeptide in the presence of the candidate agent is measured and compared with the level of ubiquitination of the substrate polypeptide in the absence of the candidate agent. A statistically significant decrease in ubiquitination of the substrate polypeptide in the presence of the candidate agent is indicative of an inhibitor of SIP-mediated ubiquitination.

The ubiquitin-conjugating system can be, e.g., a reconstituted protein mixture, a cell lysate or a whole cell. The ubiquitin-conjugating system can also include an E2 ubiquitin conjugating enzyme and/or a cullins protein. The ubiquitin can be provided in such form as (i) an unconjugated ubiquitin, in which case the ubiquitin-conjugating system further comprises an E1 ubiquitin-activating enzyme (E1), an E2 ubiquitin-conjugating enzyme (E2), and adenosine triphosphate; (ii) an activated E1: ubiquitin complex, in which case the ubiquitin-conjugating system further comprises an E2; (iii) an activated E2: ubiquitin complex; and/or (iv) an activated ubiquitin complex with the SIP ligase.

In preferred embodiments, the substrate polypeptide comprises a ubiquitination sequence of a CKI protein, e.g., a CIP/KIP protein such as p27$^{kip1}$. Likewise, preferred embodiments of the subject assay utilize cdc4 as the SIP ligase, e.g., a vertebrate cdc4, more preferably a mammalian cdc4, and even more preferably a human cdc4 ligase (such as shown in SEQ ID NO: 2).

In certain embodiments of the subject assay, at least one of the ubiquitin and the substrate polypeptide includes a detectable label, and the level of ubiquitination of the substrate polypeptide is quantified by detecting the label in at least one of the substrate polypeptide, the ubiquitin, and ubiquitin-conjugated substrate polypeptide. For illustrative purposes, the label group can be a radioisotope, a fluorescent compound, an enzyme, or an enzyme co-factor. In one embodiment, the detectable label includes a polypeptide having a measurable activity, e.g., an enzymatic activity, and the substrate polypeptide is fusion protein including the detectable label.

In other embodiments, the amount of ubiquitination of the substrate polypeptide is quantified by an immunoassay, chromatography and/or electrophoresis.

In still other embodiments, the ubiquitin-conjugating system is a host cell expressing the substrate polypeptide and SIP ligase, preferably one of the two being recombinantly produced by the cell.

In yet other embodiments of the subject assay, the reaction mixture is generated to provide a competitive binding assay, e.g., between the test agent and formation of complexes including the subject SIP polypeptides. For example, the assay can be provided as a reaction system including a substrate polypeptide and a SIP polypeptide, under wherein the substrate polypeptide and the SIP polypeptide interact. The mixture is contacted with a candidate agent, and the formation of complexes containing the substrate polypeptide and the SIP polypeptide are measured. A statistically significant decrease in the formation of complexes in the presence of the candidate agent, relative to its absence, is indicative of an inhibitor of the interaction of the substrate polypeptide and the SIP polypeptide. For such assays, the SIP polypeptide can be mutated to lack an endogenous ubiquitination activity, yet retain its ability to bind to the substrate protein.

As above, the competitive screen can be carried out as a reconstituted protein mixture, a cell lysate and/or a whole cell. In the instance of the latter, one embodiment of the subject binding assay provides the substrate and SIP polypeptides as fusion proteins in an interaction trap system.

In any embodiment of the subject assays, one or more of the compounds identified as inhibitors of the SIP-mediated ubiquitination can be formulated as a pharmaceutical preparation, e.g., for further in vivo testing and therapeutic use.

Yet another aspect of the present invention relates to diagnostic assays for determining, in the context of cells isolated from a patient, the level of a SIP transcript, SIP protein and/or SIP ligase activity, which level can be a useful diagnostic/prognostic marker for risk assessment and phenotyping cell and tissue samples. As described herein, the subject assay provides a method for determining if an animal is at risk for a disorder characterized by aberrant cell proliferation, differentiation and/or apoptosis, and also may be used for prognostic purposes when such aberrant cell phenotypes are known.

The subject method can be used for diagnosing a hyperproliferative disorder in a patient which disorder is associated with the destabilization of a CKI protein, such as p27$^{kip1}$, in cells of the patient, comprising: (i) ascertaining the level of a SIP transcript, SIP protein and/or SIP ligase activity in a sample of cells from the patient; and (ii) diagnosing the presence or absence of a hyperproliferative disorder utilizing, at least in part, the observation of upregulation of a SIP ligase, wherein an increased level of SIP expression or ligase activity in the sample, relative to a normal control sample of cells, can correlate with the presence of a hyperproliferative disorder. In another embodiment, the subject method is a prognostic method for evaluating a cancer patient's risk of death and/or recurrence of a cancer, comprising (i) ascertaining the level of expression or enyzmatic activity of a SIP ligase in a sample of cancer cells from the patient; and (ii) predicting the patient's risk of death and/or recurrence of a cancer utilizing, at least in part, that observation, wherein an increased level of expression or activation of the SIP ligase in the sample, relative to a normal control sample of cells, may correlate with an increased risk of death and/or recurrence of a cancer.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press:1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

BRIEF DESCRIPTION OF THE FIGURES

FIG. 1 shows the amino acid sequence of human cdc4 (SEQ ID NO: 2). The F box sequence is indicated by bold/italicized text; the six tandemly arranged WD40 repeals are bold-faced and underlined. The putative active site cysteine is marked with an asterisk.

FIG. 2 shows a gel of reaction products from reconstituted ubiquitin conjugating systems including human cdc4.

DETAILED DESCRIPTION OF THE INVENTION

1. General

In the eukaryotic cell cycle a key role is played by the cyclin-dependent kinases (CDKs). CDK complexes are formed via the association of a regulatory cyclin subunit and a catalytic kinase subunit. In mammalian cells, the combination of the kinase subunits (such as cdc2, CDK2, CDK4 or CDK6) with a variety of cyclin subunits (such as cyclin A, B1, B2, D1, D2, D3 or E) results in the assembly of functionally distinct kinase complexes. The coordinated activation of these complexes drives the cells through the cell cycle and ensures the fidelity of the process (Draetta, *Trends Biochem. Sci.* 15:378–382, 1990; Sherr, *Cell*

73:1059–1065, 1993). Each step in the cell cycle is regulated by a distinct and specific cyclin-dependent kinase. For example, complexes of CDK4 and D-type cyclins govern the early G1 phase of the cell cycle, while the activity of the CDK2/cyclin E complex is rate limiting for the G1 to S-phase transition. The CDK2/cyclin A kinase is required for the progression through S-phase and the cdc2/cyclin B complex controls the entry into M-phase (Sherr, *Cell* 73:1059–1065, 1993).

Cell cycle transitions are regulated by the activation and inactivation of cyclin-dependent kinases. CDKs are regulated by association with positive regulatory subunits known as cyclins, negative regulators known as CDK inhibitors (CKIs) and by phosphorylation. Recently, a link has been established between the regulation of the activity of cyclin-dependent kinases and cancer by the discovery of a group of CDK inhibitors including the $p16^{INK4a}$, $p15^{INK4b}$, $p18^{INK4c}$, $p19/p20^{INK4d}$, $p21^{Waf1/Cip1}$, $p27^{Kip1}$ and $p57^{kip2}$ proteins. These proteins, when bound to CDK complexes, inhibit their kinase activity, thereby inhibiting progression through the cell cycle. It is generally accepted that binding of these inhibitors to the CDK/cyclin complex prevents its activation. Alternatively, these inhibitors may interfere with the interaction of the enzyme with its substrates or its cofactors. The balance of these factors control CDK activity and serve to integrate signals intended to coordinate cell cycle transitions. The levels of these proteins are tightly regulated both transcriptionally and post-transcriptionally, the latter primarily achieved by regulated ubiquitin-mediated proteolysis (Pagano et al. (1995) *Science* 269:682–685; and Deschaies et al. (1995) *Curr Opin Cell Biol* 7:781–789).

The p27 protein ($p27^{Kip1}$), for instance, is a CKI protein implicated in the negative regulation of $G_1$ progression in response to a number of antiproliferative signals (Polyak et al. supra). For example, studies in macrophages have linked cyclic AMP-induced growth arrest to an increase in the amount of p27 protein, whereas the antiproliferative drug rapamycin abrogates a small reduction in p27 abundance observed after colony-stimulating factor-1 stimulation (Kato et al. (1994) *Cell* 79:487). Likewise, interleukin-2-induced proliferation of T cells results in a decrease in the amount of p27 protein, an effect that can be prevented by addition of rapamycin (Bunce et al., (1994) *Leukemia* 8:595).

The CKIs have been suggested as potential tumor suppressors since their function is often missing in transformed cells. For instance, p15 and p16 genes have been found mutated, deleted or inactivated by methylation in a large number of human malignancies. p21 is transcriptionally induced by the tumor suppressor p53, whose function is lacking in about 50% of human tumors. It has been found that in p53 minus cells, p21 is poorly expressed and is not associated with CDKs. In contrast, the p27 gene analyzed by Southern blot and PCR-SSCP in a large number of human cancers and human cell lines showed no structural alterations of point mutations (Kawamat et al. (1995) *Cancer Res* 55:2266; Ponce-Castaneda et al. (1995) *Cancer Res* 55:1211; and Pietenpol et al. (1995) *Cancer Res* 55:1206).

It has been reported that, both in vivo and in vitro, p27 is found to be degraded by the ubiquitin-dependent proteasome pathway. For instance, the human ubiquitin-conjugating enzymes Ubc2 and Ubc3 were shown to be involved in the ubiquitination of p27. Compared with proliferating cells, quiescent cells exhibited a smaller amount of p27 ubiquitinating activity, which accounted for the marked increase of p27 half-life measured in these cells. Thus, the abundance of p27 in cells is regulated by degradation. The specific proteolysis of p27 may represent a mechanism for regulating the activity of cyclin-dependent kinases. See, Pagano et al. (1995) *Science* 269: 682–685, and PCT publication WO 94/18974.

Moreover, it was also recently reported that that low cellular levels of the CDK inhibitor p27 correlate with poor prognostic outcome in colorectal and breast cancer. See U.S. Provisional Application 60/036,690 and Pagano et al. (1997) *Nature Medicine* 3:231–234. Inspection of patient samples suggested that loss of cellular p27 occurs by mechanisms operating at the post-transcriptional level, e.g., ubiquitinylation.

We have now elucidated further components to the p27 degradation pathway in mammalian cells. In particular, the present invention is based at least in part on the isolation of full length cDNAs encoding vertebrate proteins which are involved in ubiquitinylation of substrate proteins, thereby resulting in the proteolysis of the substrate proteins.

As described with greater detail below, we have identified metazoan homologs, particularly mammalian homologs of the yeast cdc4 protein. These proteins, referred to herein as "hu-cdc4" for the human homolog (SEQ ID NOs: 1 and 2), and "mu-cdc4" for the mouse homolog (SEQ ID NOs: 3 and 4), were initially identified on the basis of their ability to interact with the human protein $p19^{skp1}$. The mammalian cdc4 proteins include an F box, a domain which has been shown to mediate the interaction between cdc4 proteins and skp1 proteins in yeast (Bori et al. (1996) *Cell* 86:263). The F box is located in a region corresponding to residues 243–285 of SEQ ID NO: 2. Moreover, the mammalian cdc4 proteins are characterized by six WD-40 repeats, which in other proteins have been suggested to serve as a platform for protein-protein interactions (Sondek (1996) *Nature* 379:369). These repeats are located from residues between approximately residues 642–1073 of SEQ ID NO: 2. In particular, those six repeats (see FIG. 1) are located at residues 642–683, 684–782, 783–845, 846–945, 946–1040 and 1041–1073. Based on sequence conservation, the active site cysteine is likely to be Cys-813. The human cdc4 has an apparent core polypeptide molecular weight of 122 kD.

As demonstrated in Table 1, the vertebrate homologs of cdc4, while related to one and other, are substantially different in sequence from the yeast cdc4 protein.

TABLE 1

| | Percent Identity, protein sequence | | | |
|---|---|---|---|---|
| 1 | 2 | 3 | | |
| 82.0 | 10.8 | | 1 | human cdc4 |
| | 14.3 | | 2 | mouse cdc4 |
| | | | 3 | S. Cerevisae cdc4 |

Indeed, the subject mouse and human cdc4 proteins define a new family of ubiquitin ligases. Certain of the ubiquitin ligases (E3s) contain a carboxyl terminal "HECT" domain—for homologous to E6-AP carboxyl terminus—see Huibregtse et al. (1995) *PNAS* 92:2563–2567). The subject E3 ligases, of which cdc4 is an archeotype, are referred to herein as "SIP ligases" for Skp Interacting Proteins. The full-length SIP ligases contain two recognizable sequence motifs that are found in many unrelated proteins: an F box, which serves as an interaction domain for SKP1 (Bai et al. (1996) (*cell* 86:263), and six WD-40 repeats (Neer et al. (1994) *Nature* 371:297), which may serve as a platform for protein-protein interaction (Sondek et al. (1996) *Nature* 379:369). The portion of the cdc4 protein bounded by the WD40 motifs flanking both sides of the putative active site cysteine (see FIG. 1) are referred to herein as a "SIP domain", e.g., corresponding approximately residues 642–1073 of SEQ ID NO: 2.

The yeast homologs of cdc4 has been shown to be involved in protein degradation by the ubiquitination pathway, and in particular, the degradation of proteins involved in cell cycle regulation. For instance, the yeast cdc4 protein has been involved in degradation of multiple cell cycle regulators, including the G1 cyclins Cln2 and Cln3, Far1, and Sic1 (summarized in Mathias et al. (1996) *Mol. Cell. Biol.* 16:6634). Cdc4 is involved in protein degradation in association with the ubiquitin conjugating enzyme cdc34, which is capable of catalyzing the degradation of several cell cycle regulators, including the yeast cyclin-dependent kinase inhibitor p40$^{sic1}$, the degradation of which is required for DNA replication.

Based at least in part on the fact that in yeast (i) the yeast cdc4 protein has been implicated in ubiquitinylation; and (ii) the yeast cdc4 protein is capable of interacting with the ubiquitin conjugating enzyme cdc34 and with skp1, which is required for ubiquitination and degradation of cell cycle regulatory proteins, it is likely that yeast cdc4 is capable of acting as, or forming, a ubiquitin ligase, e.g., an E3 ligase, which is capable of ubiquitinylating substrate proteins, such as cell cycle regulatory proteins (Bai et al. (1996) *Cell* 86:263; Mathias et al. (1996) *Mol. Cell. Biol.* 16:6634). Based on both biochemical/biological data, and analogy to the yeast system, the subject vertebrate cdc4 protein is understood to be involved in the ubiquitinylation of proteins in vertebrate cells.

Accordingly, the present invention provides nucleic acids and the proteins which function in the ubiquitinylation of substrate proteins. The invention also provides methods for modulating protein degradation, assays for identifying compounds which modulate protein degradation, methods for treating disorders associated with aberrant protein degradation, diagnostic and prognostic assays for determining whether a subject is at risk of developing a disorder associated with an aberrant protein degradation. Furthermore, based at least on the observation that vertebrate homologs of cdc4 are presumably involved in the degradation of cell cycle regulatory proteins, e.g., p27 and the like, and G1 phase cyclins (such as cyclin D1, D2, D3 or E), the invention also provide methods for modulating cell proliferation, differentiation, and survival.

The present invention also provides diagnostic and prognostic assays for determining whether a subject is at risk of developing a disorder associated with an aberrant cell proliferation, differentiation, and/or survival. For instance, we have observed that transcription of the cdc4 gene is upregulated in tissues where the intracellular level of p27$^{KIP1}$ is low.

2. Definitions

For convenience, certain terms employed in the specification, examples, and appended claims are collected here.

The terms "SIP polypeptide" and "SIP protein", as used herein, refer to a class of polypeptides which mediate ubiquitination of a substrate protein. In this regard, the SIP polypeptide may be a ubiquitin ligase, e.g., itself be capable of catalyzing the transfer of a ubiquitin from an E2 enzyme to a substrate protein (as a ligase). Alternatively, the SIP polypeptide may be an auxiliary substrate recognition protein, acting as a chaperon for formation of complexes including the substrate protein and a ubiquitin ligase and/or a ubiquitin conjugating enzyme. As will generally be clear from the context in which it is used in the present application, the term SIP polypeptide will typically refer to the subject vertebrate SIP ligases.

The terms "SIP protein" and "SIP ligase", used interchangeably herein, refer to a family of ubiquitin ligases characterized by a series of WD40 motifs flanking the likely active site cysteine. There can be from 2 to 10 WD40 repeats, though 2–5 are the preferred embodiments. The cdc4 protein of SEQ ID NO: 2 is prototypical of the SIP ligase family, and has 4 WD40 repeats, e.g., the SIP domain is generally represented by the formula WD40-WD40-Cys*-WD40-WD40 (where Cys* represents the putative active site cysteine).

A "WD-40 motif", also referred to in the art as "β-transducin repeats" or "WD-40 repeats", is roughly defined as a contiguous sequence of about 25 to 50 amino acids with relatively-well conserved sets of amino acids at the two ends (amino- and carboxyl-terminal) of the sequence. For review, see Simon et al. (1991) *Science* 252:802–808; and Neer et al. (1994) *Nature* 371:297. Conserved sets of at least one WD-40 repeat of a WD-40 repeat-containing protein typically contain conserved amino acids at certain positions. The amino-terminal set, comprised of two contiguous amino acids, often contains a Gly followed by a His. The carboxyl-terminal set, comprised of six to eight contiguous amino acids, typically contains an Asp at its first position, and a Trp followed by an Asp at its last two positions.

A more accurate definition of a WD-40 motif incorporates the observation that while specific residues, such as those identified above, are not always conserved within a WD-40 motif, conserved positions within the motif are typically occupied by residues selected from a restricted class of amino acids.

In order to better define the class of conserved residues at selected positions, it is necessary to group amino acids on the basis of certain common properties. A functional way to define common properties between individual amino acids is to analyze the normalized frequencies of amino acid changes between corresponding proteins of homologous organisms (Schulz). According to such analyses, groups of amino acids may be defined where amino acids within a group exchange preferentially with each other, and therefore resemble each other most in their impact on the overall protein structure (Schulz). Examples of amino acid groups defined in this manner, some of which are used in the definition of a WD-40 motif herein, include:

(i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp, (v) a nitrogen ring group, consisting of His and Trp, (vi) a large aliphatic nonpolar group, consisting of Val, Leu and Ile, (vii) a slightly-polar group, consisting of Met and Cys, (viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr.

In addition to the groups presented above, each amino acid residue may form its own group, and the group formed by an individual amino acid may be referred to simply by the one and/or three letter abbreviation for that amino acid commonly used in the art.

Thus, a "WD-40" motif is defined herein as a contiguous set of amino acids between (inclusive) two sets of relatively well conserved residues, termed herein as an "amino-terminal set" and a "carboxyl-terminal set". The amino-terminal set contains two adjacent amino acids. The residue at the first position is typically selected from groups ii, vi or viii, while the residue at the second position is typically selected from groups i, x or Ile. The first and second positions will often consist of Gly and His, respectively. The Gly and His residues are typically present in at least one of the aligned repeats of a WD-40-containing protein.

The carboxyl-terminal conserved set typically includes eight residues, but may contain as few as six residues. The most well-conserved residue in WD-40 motifs identified thus far is an Asp residue, comprising the first amino acid of the carboxyl-terminal conserved set. It is present in virtually all WD-40 repeats illustrated herein. In those repeats where it is not present, the position is occupied by a residue from groups iii or Gly.

The last two amino acids in the carboxyl-terminal conserved set are typically selected from groups iv or Ile, and groups i or viii, respectively. The most commonly used residue at the first of these positions is Trp. It is typically present in at least one of the WD-40 repeats of any given protein. The second position is occupied less consistently by a single residue, but is often occupied by Asp. The Trp-Asp (WD) combination is part of the namesake of WD-40 repeats.

The amino acids present in the internal portion of the carboxyl-terminal conserved set are less well-conserved than the terminal residues, and their total number may differ by up to two residues in different WD-40 repeats. The third position in from the carboxyl-terminal end of the carboxyl-terminal conserved set is typically selected from groups viii or ix, more typically ix. The fifth position in from the carboxyl-terminal end of the carboxyl-terminal conserved set is also typically selected from groups viii or ix, more typically ix.

The length of a WD-40 repeat, including the amino-terminal and carboxyl-terminal conserved sets is typically between about 25 and about 50 residues, more typically between about 29 and 34 residues. The distribution arises primarily from differences in the number of residues present between the amino-terminal and carboxyl-terminal conserved sets.

Thus, according to, e.g., Neer et al., a general formula for characterizing a WD40 repeat is $$\{X_{6-94}\text{-}[GH\text{-}X_{23-41}\text{-}WD]\}_N$$

wherein $X_{6-94}$ represents from 6 to 94 contiguous amino acid residues, $X_{23-41}$ represents from 23 to 41 contiguous amino acid residues, and N represents an integer from 4–8. Other WD40 repeats will, however, be appreciated by those skilled in the art.

Other types of searches may be equally effective at identifying proteins which may contain WD-40 repeats. For example, on-line databases such as GenBank or SwissProt can be searched, either with an entire sequence of a WD-40-containing protein, or with a consensus WD-40 repeat sequence. Various search algorithms and/or programs may be used, including FASTA, BLAST or ENTREZ. FASTA and BLAST are available as a part of the GCG sequence analysis package (University of Wisconsin, Madison, Wis.). ENTREZ is available through the National Center for Biotechnology Information, National Library of Medicine, National Institutes of Health, Bethesda, Md.

The number of WD-40 repeats in a particular protein can range from two to more than eight.

The term "cdc53" is used interchangeably herein with the term "cullins" when referring to a vertebrate homolog of the yeast cdc53 protein. The term "cullins polypeptide" or "cullins protein", refers to a member of the cullins family, e.g., any one of cul–1, –2, –3, –4, –5, or –6.

"Biological activity" or "bioactivity" or "activity" or "biological function", which are used interchangeably, for the purposes herein means an effector or antigenic function that is directly or indirectly performed by a SIP polypeptide (whether in its native or denatured conformation), or by any subsequence thereof. Biological activities include binding to another protein, such as another E3 polypeptide, an E2 conjugating enzyme, a skp1 protein, a skp2 protein, a ubiquitin conjugating enzyme, and/or a substrate protein. In particular, the biological activity of a SIP ligase of the invention can be binding of the protein to a cullins protein, a skp1 protein, a ubiquitin conjugating enzyme or a substrate protein such as p27. The biological activity of a SIP polypeptide can also include the ability to mediate ubiquitination of a substrate protein, such as when the SIP polypeptide is associated with other proteins, e.g., other components of an E3 complex (e.g., cdc53 homologs) and skp proteins. The biological activity of an SIP polypeptide can also include: an ability to regulate the cell-cycle of an eukaryotic cell; an ability to modulate proliferation/cell growth, differentiation, and/or survival of an eukaryotic cell; an ability to modulate entry of a mammalian or yeast cell into S or M phase; an ability to ubiquitinate a cell-cycle regulator, e.g. p27. The SIP polypeptides of the present invention may also function to modulate differentiation of cells/tissue and cell death.

Biologically active SIP polypeptides include polypeptides having both an effector and antigenic function, or only one of such functions. The term "SIP ligase" also includes antagonist polypeptides and native SIP proteins, provided that such antagonists include an epitope of a native SIP ligase.

As used herein the term "bioactive fragment of a SIP protein" refers to a fragment of a full-length SIP protein, wherein the fragment specifically mimics or antagonizes the activity of a wild-type SIP protein. The bioactive fragment preferably is a fragment capable of binding to a second protein, e.g., another protein involved in ubiquitin conjugation.

A "ubiquitination sequence" refers to a portion of a protein which is sufficient to cause SIP ligase-mediated ubiquitination of the protein.

The term "an aberrant activity", as applied to an activity of a SIP ligase, refers to an activity which differs from the activity of the wild-type or native protein or which differs from the activity of the protein in a healthy subject. An activity of a protein can be aberrant because it is unregulated, e.g., constitutively activated or inactivated, relative to its native counterpart. An aberrant activity can also be a change in an activity. For example an aberrant protein can interact with a different protein relative to its native counterpart. A cell can also have an aberrant SIP activity due to overexpression or underexpression of the gene encoding an SIP polypeptide.

The term "SIP therapeutic" refers to various forms of SIP polypeptides, as well as peptidomimetics, small molecules, nucleic acids, and antibodies, which can modulate at least one activity of a SIP protein, e.g., binding to another protein, by mimicking or potentiating (agonizing) or inhibiting (antagonizing) the effects of a naturally-occurring SIP protein, inhibiting an enzymatic activity of the ligase (such as ubiquitin ligase activity), or inhibits expression of a SIP protein. A SIP therapeutic which mimics or potentiates the activity of a wild-type SIP protein is a "SIP agonist". Conversely, a SIP therapeutic which inhibits the activity of a wild-type SIP ligase is a "SIP antagonist".

The terms peptides, proteins and polypeptides are used interchangeably herein.

Polypeptides referred to herein as possessing the activity of "ubiquitination", e.g., such as with regard to the activity of a "ubiquitin-conjugating enzyme" or "ubiquitin ligase", are understood to be capable of forming a thiol ester adduct with the C-terminal carboxyl group of ubiquitin and transferring the ubiquitin to an $\epsilon$-amino group in an acceptor protein by formation of an isopeptide bond.

The term "E3 complex" refers to a protein complex including the subject SIP ligase, e.g., cdc4, which protein complex augments or otherwise facilitates the ubiquitination of a protein. In preferred embodiments, the E3 complex mediates the ubiquitination of a cell cycle regulatory protein, e.g., cyclin-dependent kinase inhibitors such as $p27^{kip1}$ or $p57^{kip2}$.

As used herein "SIP-dependent ubiquitination" refers to the conjugation of ubiquitin to a protein by a mechanism which requires a SIP protein or SIP-containing protein complex, e.g., which is dependent on the presence of a SIP ligase.

The term "substrate protein" or "target protein" refers to a protein, preferably a cellular protein, which can be ubiquitinated by an SIP-dependent reaction pathway.

The term "CKI protein" refers to a protein which is an inhibitor of CDK activation. Exemplary CKI proteins include members of the CIP/KIP family, such as $p21^{CIP1}$, $p27^{KIP1}$, and $p57^{KIP2}$, and members of the INK4 family, such as $p16^{INK4A}$ or $p15^{INK4B}$.

The term "CIP/KIP protein" refers to members of another CKI protein family which includes $p27^{KIP1}$ (Polyak et al. (1994) *Cell* 78:67–74); $p21^{CIP1}$ (WAF1/SDI1/CAP20; Xiong et al. (1993) *Nature* 366:701–704); and $p57^{KIP2}$ (Lee et al. (1995) *Genes Dev.* 9:639–649; and Matsuoka et al. (1995) *Genes Dev.* 9:650–662). In addition to the functional characteristic of CDK inhibition, the CIP/KIP proteins each have a CDK inhibitory motif (a CDK-binding motif) of about 50 amino acids, referred to herein as a "p21/p27" inhibitory domain, which is conserved in members of the CIP/KIP family.

The term "INK4 protein" refers to a family of structurally related CDK inhibitors characterized by a fourfold repeated ankyrin-like sequence (Elledge et al. (1994) *Curr. Opin. Cell Biol.* 6:874–878), and the ability to bind to CDKs, especially CDK4 and CDK6. Exemplary members of this protein family include p16 (INK4A/MTS1; Serrano et al (1993) *Nature* 366:704–707); p15 (INK4B; Hannon et al. (1994) *Nature* 371:257–261); p18 (INK4c; Guan et al. (1994) *Genes Dev.* 8:2939–2952) and p19/p20 (INK4d; Chan et al. (1995) *Mol. Cell Biol.* 15:2682–2688; and Hirai et al. (1995) *Mol. Cell Biol.* 15:2672–2681).

A "cyclin dependent kinase" or "CDK" are art recognized terms referring to protein of the family of proteins which include catalytic subunits of cyclin/CDK complexes. Exemplary CDK proteins include CDC2, CDK2, CDK3, CDK4, CDK5, CDK6 and CDK7. The sequence for wild-type CDK protein can be found, in GenBank.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

As used herein, the term "gene" or "recombinant gene" refers to a nucleic acid comprising an open reading frame encoding a SIP polypeptide of the present invention, including both exon and (optionally) intron sequences. A "recombinant gene" refers to nucleic acid encoding a SIP polypeptide and comprising SIP-encoding exon sequences, though it may optionally include intron sequences which are either derived from a chromosomal SIP ligase gene or from an unrelated chromosomal gene. An exemplary recombinant gene encoding the subject hu-cdc4 polypeptide is represented by SEQ ID NO: 1. The term "intron" refers to a DNA sequence present in a given SIP gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a SIP polypeptide of the present invention or where anti-sense expression occurs from the transferred gene, the expression of a naturally-occurring form of the SIP gene is disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant SIP ligase gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the SIP protein.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a urogenital origin, e.g. renal cells, or cells of a neural origin, e.g. neuronal cells. The term also covers so-called "leaky" promoters, which regulate expression of a selected DNA primarily in one tissue, but cause expression in other tissues as well.

As used herein, a "transgenic animal" is any animal, preferably a non-human mammal, a bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of a SIP protein, e.g. either agonistic or antagonistic forms. However, transgenic animals in which the recombinant SIP gene is silent are also contemplated, as for example, the FLP or CRE recombinase dependent constructs described below.

The "non-human animals" of the invention include vertebrates such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding, for example, embryogenesis and tissue patterning. The term "chimeric animal" is used herein to refer to animals in which the recombinant gene is found, or in which the recombinant is expressed in some but not all cells of the animal. The term "tissue-specific chimeric animal" indicates that the recombinant SIP gene is present and/or expressed in some tissues but not others.

As used herein, the term "transgene" means a nucleic acid sequence (encoding, e.g., a SIP polypeptide), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a SIP polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, though preferably less than 25% identity with a SIP ligase sequence of the present invention.

Polypeptides referred to herein as mammalian homologs of Cdc4 further refers to other mammalian paralogs, or other mammalian orthologs.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding a SIP polypeptide with a second amino acid sequence defining a domain foreign to and not substantially homologous with any domain of the SIP protein. A chimeric protein may present a foreign domain which is found (albeit in a different protein) in an organism which also expresses the first protein, or it may be an "interspecies", "intergenic", etc. fusion of protein structures expressed by different kinds of organisms.

The term "isolated" as also used herein with respect to nucleic acids, such as DNA or RNA, refers to molecules separated from other DNAs, or RNAs, respectively, that are present in the natural source of the macromolecule. For example, isolated nucleic acids encoding a SIP polypeptides preferably include no more than 10 kilobases (kb) of nucleic acid sequence which naturally immediately flanks particular SIP gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

The term "whole lysate" refers to a cell lysate which has not been manipulated, e.g. either fractionated, depleted or charged, beyond the step of merely lysing the cell to form the lysate. The term whole cell lysate does not, however, include lysates derived from cells which produce recombinant forms of one or more of the proteins required to constitute a ubiquitin-conjugating system for SIP-dependent ubiquitination of a substrate protein.

The term "charged lysate" refers to cell lysates which have been spiked with exogenous, e.g., purified, semi-purified and/or recombinant, forms of one or more components of an SIP-dependent ubiquitin-conjugating system, or the substrate protein thereof. The lysate can be charged after the whole cells have been harvested and lysed, or alternatively, by virtue of the cell from which the lysate is generated expressing a recombinant form of one or more of the conjugating system components.

The term "semi-purified cell extract" or, alternatively, "fractionated lysate", as used herein, refers to a cell lysate which has been treated so as to substantially remove at least one component of the whole cell lysate, or to substantially enrich at least one component of the whole cell lysate. "Substantially remove", as used herein, means to remove at least 10%, more preferably at least 50%, and still more preferably at least 80%, of the component of the whole cell lysate. "Substantially enrich", as used herein, means to enrich by at least 10%, more preferably by at least 30%, and still more preferably at least about 50%, at least one component of the whole cell lysate compared to another component of the whole cell lysate. The component which is removed or enriched can be a component of a ubiquitin-conjugation pathway, e.g., ubiquitin, a substrate protein, an E1, an E2, or SIP protein(s), and the like, or it can be a component which can interfere with a ubiquitin-binding assay, e.g., a protease.

The term "semi-purified cell extract" is also intended to include the lysate from a cell, when the cell has been treated so as to have substantially more, or substantially less, of a given component than a control cell. For example, a cell which has been modified (by, e.g., recombinant DNA techniques) to produce none (or very little) of a component of a ubiquitin-conjugation pathway, will, upon cell lysis, yield a semi-purified cell extract.

The term "component of a ubiquitin-conjugation pathway", as used herein, refers to a component which can participate in the ubiquitination of a substrate protein either in vivo or in vitro. Exemplary components of a ubiquitin-conjugation pathway include ubiquitin, an E1, an E2, a SIP protein or protein complex, a substrate protein, and the like.

By "semi-purified", with respect to protein preparations, it is meant that the proteins have been previously separated from other cellular or viral proteins. For instance, in contrast to whole cell lysates, the proteins of reconstituted conjugation system, together with the substrate protein, can be present in the mixture to at least 50% purity relative to all other proteins in the mixture, more preferably are present at at least 75% purity, and even more preferably are present at 90–95% purity.

The term "purified protein", with respect to components of the ubiquitination pathway, refers to a preparation of a protein or proteins which are preferably isolated from, or otherwise substantially free of, other proteins normally associated with the protein(s) in a cell or cell lysate. The term "substantially free of other cellular proteins" (also referred to herein as "contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene as described in the attached examples. By "purified", it is meant, when referring to the component proteins preparations used to generate the reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either protein in its native state (e.g. as a part of a cell), or as part of a cell lysate, or that have been separated into components (e.g., in an acrylamide gel) but not obtained either as pure (e.g. lacking contaminating proteins) substances or solutions. The term isolated as used herein also refers to a component protein that is substantially free of cellular material or culture medium when produced by recombinant DNA techniques, or chemical precursors or other chemicals when chemically synthesized.

The term "recombinant protein" refers to a protein of the present invention which is produced by recombinant DNA techniques, wherein generally DNA encoding the expressed protein is inserted into a suitable expression vector which is in turn used to transform a host cell to produce the heterologous protein. Moreover, the phrase "derived from", with respect to a recombinant gene encoding the recombinant protein is meant to include within the meaning of "recombinant protein" those proteins having an amino acid sequence of a native protein, or an amino acid sequence similar thereto which is generated by mutations including substitutions and deletions of a naturally occurring protein.

As used herein, a "reporter gene construct" is a nucleic acid that includes a "reporter gene" operatively linked to a transcriptional regulatory sequence. Transcription of the reporter gene is controlled by these sequences. The activity of at least one or more of these control sequences is directly or indirectly regulated by a signal transduction pathway involving an ubiquitin substrate protein of the subject SIP proteins. The transcriptional regulatory sequences can include a promoter and other regulatory regions, such as enhancer sequences, that modulate the level of expression of a reporter gene in response to the level of a substrate protein.

As used herein, the term "specifically hybridizes" refers to the ability of a nucleic acid probe/primer of the invention to hybridize to at least 15, 25, 50 or 100 consecutive nucleotides of a target gene sequence, or a sequence complementary thereto, or naturally occurring mutants thereof, such that it has less than 15%, preferably less than 10%, and more preferably less than 5% background hybridization to a cellular nucleic acid (e.g., mRNA or genomic DNA) other than the target gene.

As used herein, "phenotype" refers to the entire physical, biochemical, and physiological makeup of a cell, e.g., having any one trait or any group of traits.

"Small molecule" as used herein, is meant to refer to a composition, which has a molecular weight of less than about 5 kD and most preferably less than about 2.5 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention.

3. SIP Ligase Nucleic Acids and Expression Vectors

As described below, one aspect of the invention pertains to isolated nucleic acid having a nucleotide sequence encoding a SIP protein, e.g., a vertebrate SIP ligase such as cdc4 and/or equivalents of such nucleic acids. The term nucleic acid as used herein is intended to include fragments and equivalents. The term equivalent is understood to include nucleotide sequences encoding functionally equivalent SIP proteins or functionally equivalent polypeptides which, for example, retain the ability to bind to another protein, such as another component of an E3 complex, such as skp1, or a substrate protein such as p27. Equivalent nucleotide sequences will include sequences that differ by one or more nucleotide substitutions, additions or deletions, such as allelic variants; and will, therefore, include coding sequences that differ from the nucleotide sequence of the human cdc4 gene coding sequence shown in SEQ ID No: 1, e.g., due to the degeneracy of the genetic code. Equivalents will also include nucleotide sequences that hybridize under stringent conditions (i.e., equivalent to about 20–27° C. below the melting temperature ($T_m$) of the DNA duplex formed in about 1 M salt) to the nucleotide sequence of an coding sequence represented in in SEQ ID NO: 1 or 3. In one embodiment, equivalents will further include nucleic acid sequences derived from and evolutionarily related to a nucleotide sequence shown in SEQ ID NO: 1 or 3.

Moreover, it will be generally appreciated that, under certain circumstances, it may be advantageous to provide homologs of the subject SIP proteins, which homologs function in a limited capacity as one of either an agonist (mimetic) or an antagonist in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of a SIP protein's biological activities. For instance, antagonistic homologs can be generated which interfere with the ability of the wild-type ("authentic") SIP protein to associate with other proteins in the ubiquintination pathway, but which do not substantially interfere with the formation of complexes between the native SIP protein and other cellular proteins, such as may be involved in other regulatory mechanisms of the cell.

Polypeptides referred to herein as SIP polypeptides preferably have an amino acid sequence corresponding to all or a portion of the SIP amino acid sequence shown in SEQ ID NO: 2 or 4, or are homologous with one of these proteins, such as other human paralogs, or mammalian orthologs.

In general, the biological activity of a SIP polypeptide will be characterized as including the ability, in the presence of other required proteins, to mediate and/or catalyze the transfer a ubiquitin molecule from a relevant ubiquitin conjugating enzyme (UBC) to a lysine residue of its substrate protein. The above notwithstanding, the biological activity of a SIP polypeptide may be characterized by one or more of the following attributes: an ability to regulate the cell-cycle of an eukaryotic cell, especially a mammalian cell (e.g., of a human cell), or a yeast cell such as a Schizosaccharomyces cell; an ability to modulate proliferation/cell growth of a eukaryotic cell; an ability to modulate entry of a mammalian or yeast cell into S phase; an ability to ubiquitinate a cell-cycle regulator, e.g. a cyclin dependent kinase inhibitor, e.g., p27. The SIP polypeptides of the present invention may also function to modulate differentiation of cells/tissue. The subject polypeptides of this invention may also be capable of modulating cell growth or proliferation by influencing the action of other cellular proteins. A SIP polypeptide can be a specific agonist of the function of the wild-type form of the protein, or can be a specific antagonist, such as a catalytically inactive mutant. Other biological activities of the subject SIP proteins are described herein, or will be reasonably apparent to those skilled in the art in light of the present disclosure.

In one embodiment, the nucleic acid of the invention encodes a polypeptide which is an agonist or antagonist of a naturally occurring vertebrate SIP gene product, such as a cdc4 protein, and comprises an amino acid sequence having a SIP motif (supra). Preferred SIP proteins are identical or homologous to the amino acid sequence represented in SEQ ID NO: 2 or 4. Preferred nucleic acids encode a polypeptide at least 60% homologous, more preferably 70% homologous and most preferably 80% homologous with an amino acid sequence shown in SEQ ID NO: 2 or 4 Nucleic acids which encode polypeptides having an activity of a cdc4 protein and having at least about 90%, more preferably at least about 95%, and most preferably at least about 98–99% homology with a sequence shown in SEQ ID NO: 2 or 4 are also within the scope of the invention. Preferably, the nucleic acid is a cDNA molecule comprising at least a portion of the nucleotide sequence encoding a human cdc4 protein shown in SEQ ID NO: 2. A preferred portion of the cDNA molecule designated by SEQ ID NO: 1 includes the coding region of the molecule.

Isolated nucleic acids which differ from the nucleotide sequences shown in SEQ ID NO: 1 or 3 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject SIP proteins will exist among mammalian cells. One skilled in the art will appreciate that these variations in one or more nucleotides (up to about 3–5% of the nucleotides) of the nucleic acids encoding a particular SIP protein may exist among individuals of a given species due to natural allelic variation. Any and all such nucleotide variations and resulting amino acid polymorphisms are within the scope of this invention.

The present invention pertains to nucleic acids encoding SIP proteins derived from an eukaryotic cell and which have amino acid sequences evolutionarily related to a SIP protein represented by SEQ ID NO: 2 or 4 wherein "evolutionarily related to", refers to SIP proteins having amino acid sequences which have arisen naturally (e.g. by allelic variance or by differential splicing), as well as mutational variants of SIP proteins which are derived, for example, by combinatorial mutagenesis.

Fragments of the nucleic acid encoding a biologically active portion of the subject SIP proteins are also within the scope of the invention. As used herein, a fragment of the nucleic acid encoding an active portion of a SIP protein refers to a nucleotide sequence having fewer nucleotides than the nucleotide sequence encoding the full length amino acid sequence of, for example, the SIP protein represented in SEQ ID NO: 2, and which encodes a polypeptide which retains at least a portion of the biological activity of the full-length protein as defined herein, or alternatively, which is functional as an antagonist of the biological activity of the full-length protein. For example, such fragments include, as appropriate to the full-length protein from which they are derived, a polypeptide containing a domain mediating the interaction of the SIP protein with another protein. For example, a biologically active portion of a SIP ligase can be a portion of a cdc4 protein of the invention which is capable of interacting with a cullins protein, with a ubiquitin conjugating enzyme, with a skp1 protein and/or with a substrate protein. Particularly preferred biologically active portions of vertebrate SIP proteins of the invention include the WD repeats, which are located between approximately residues 642–1073 of SEQ ID NO: 2, and (though optionally) the F box, which corresponds to from about residues 243–285 of SEQ ID NO: 2. In preferred embodiments, the active portion also includes an active site cysteine, such as Cys-813 of SEQ ID NO: 2. The corresponding domains in other cdc4 homologs can be identified by sequence comparison with the human cdc4 protein. Other preferred domains of cdc-4 include domains of the protein which mediate interaction with yet other proteins.

Nucleic acids within the scope of the invention may also contain linker sequences, modified restriction endonuclease sites and other sequences useful for molecular cloning, expression or purification of such recombinant polypeptides.

As indicated by the examples set out below, a nucleic acid encoding a SIP polypeptide may be obtained from mRNA or genomic DNA from any vertebrate organism in accordance with protocols described herein, as well as those generally known to those skilled in the art. A cDNA encoding a SIP polypeptide, for example, can be obtained by isolating total mRNA from a cell, e.g. a mammalian cell, e.g. a human cell. Double stranded cDNAs can then be prepared from the total mRNA, and subsequently inserted into a suitable plasmid or bacteriophage vector using any one of a number of known techniques. A gene encoding a SIP protein can also be cloned using established polymerase chain reaction techniques in accordance with the nucleotide sequence information provided by the invention.

Another aspect of the invention relates to the use of the isolated nucleic acid in "antisense" therapy. As used herein, antisense therapy refers to administration or in situ generation of oligonucleotide probes or their derivatives which specifically hybridize (e.g. binds) under cellular conditions with the cellular mRNA and/or genomic DNA encoding one of the subject SIP proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, antisense therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a SIP protein. Alternatively, the antisense construct is an oligonucleotide probe which is generated ex vivo and which, when introduced into the cell causes inhibition of expression by hybridizing with the mRNA and/or genomic sequences encoding a SIP protein. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der Krol et al., (1988) *Biotechniques* 6:958–976; and Stein et al., (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of modes of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind, such as for determining the level of expression of a gene of the invention or for determining whether a gene of the invention contains a genetic lesion.

In another aspect of the invention, the subject nucleic acid is provided in an expression vector comprising a nucleotide sequence encoding a subject SIP polypeptide and operably linked to at least one regulatory sequence. Operably linked is intended to mean that the nucleotide sequence is linked to a regulatory sequence in a manner which allows expression of the nucleotide sequence. Regulatory sequences are art-recognized and are selected to direct expression of the polypeptide having an activity of a SIP ligase. Accordingly, the term regulatory sequence includes promoters, enhancers and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding the SIP proteins of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

As will be apparent, the subject gene constructs can be used to cause expression of the subject SIP polypeptides in cells propagated in culture, e.g. to produce proteins or polypeptides, including fusion proteins or polypeptides, for purification.

This invention also pertains to a host cell transfected with a recombinant SIP gene in order to express a polypeptide having an activity of a SIP ligase. The host cell may be any prokaryotic or eukaryotic cell. For example, a SIP polypeptide of the present invention may be expressed in bacterial cells such as *E. coli*, insect cells (baculovirus), yeast, or mammalian cells. Other suitable host cells are known to those skilled in the art.

Accordingly, the present invention further pertains to methods of producing the subject SIP polypeptides. For example, a host cell transfected with an expression vector encoding a SIP polypeptide can be cultured under appropriate conditions to allow expression of the polypeptide to occur. The polypeptide may be secreted and isolated from a mixture of cells and medium containing the polypeptide. Alternatively, the polypeptide may be retained cytoplasmically and the cells harvested, lysed and the protein isolated. A cell culture includes host cells, media and other byproducts. Suitable media for cell culture are well known in the art. The polypeptide can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the SIP protein. In a preferred embodiment, the SIP protein is a fusion protein containing a domain which facilitates its purification, such as an SIP-GST fusion protein.

Thus, a nucleotide sequence derived from the cloning of the SIP proteins described in the present invention, encoding all or a selected portion of the protein, can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures. Similar procedures, or modifications thereof, can be employed to prepare recombinant SIP proteins, or portions thereof, by microbial means or tissue-culture technology in accord with the subject invention.

The recombinant SIP protein can be produced by ligating the cloned gene, or a portion thereof, into a vector suitable for expression in either prokaryotic cells, eukaryotic cells, or both. Expression vehicles for production of a recombinant SIP protein include plasmids and other vectors. For instance, suitable vectors for the expression of a SIP protein include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al., (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant SIP protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When expression of a carboxy terminal fragment of the full-length SIP proteins is desired, i.e. a truncation mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., (1987) *J. Bacteriol.* 169:751–757) and *Salmonella typhimurium* and its in vitro activity has been demonstrated on recombinant proteins (Miller et al., (1987) *PNAS USA* 84:2718–1722). Therefore, removal of an N-terminal methionine, if desired, can be achieved either in vivo by expressing such recombinant polypeptides in a host which produces MAP (e.g., *E. coli* or CM89 or *S. cerevisiae*), or in vitro by use of purified MAP (e.g., procedure of Miller et al.).

Alternatively, the coding sequences for the polypeptide can be incorporated as a part of a fusion gene including a nucleotide sequence encoding a different polypeptide. This type of expression system can be useful under conditions where it is desirable, e.g., to produce an immunogenic fragment of the SIP protein. For example, the VP6 capsid protein of rotavirus can be used as an immunologic carrier protein for portions of polypeptide, either in the monomeric form or in the form of a viral particle. The nucleic acid sequences corresponding to the portion of the SIP protein to which antibodies are to be raised can be incorporated into a fusion gene construct which includes coding sequences for a late vaccinia virus structural protein to produce a set of recombinant viruses expressing fusion proteins comprising a portion of the protein as part of the virion. The Hepatitis B surface antigen can also be utilized in this role as well.

Similarly, chimeric constructs coding for fusion proteins containing a portion of a SIP protein and the poliovirus capsid protein can be created to enhance immunogenicity (see, for example, EP Publication No. 0259149; and Evans et al., (1989) *Nature* 339:385; Huang et al., (1988) *J. Virol.* 62:3855; and Schlienger et al., (1992) *J. Virol.* 66:2).

The Multiple Antigen Peptide system for peptide-based immunization can be utilized, wherein a desired portion of a SIP protein is obtained directly from organo-chemical synthesis of the peptide onto an oligomeric branching lysine core (see, for example, Posnett et al., (1988) *JBC* 263:1719 and Nardelli et al., (1992) *J. Immunol.* 148:914). Antigenic determinants of the SIP protein can also be expressed and presented by bacterial cells.

In addition to utilizing fusion proteins to enhance immunogenicity, it is widely appreciated that fusion proteins can also facilitate the expression of proteins. For example, the SIP protein of the present invention can be generated as a glutathione-S-transferase (GST) fusion proteins. Such GST fusion proteins can be used to simply purification of the SIP protein, such as through the use of glutathione-derivatized matrices (see, for example, *Current Protocols in Molecular Biology*, eds. Ausubel et al., (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a $Ni^{2+}$ metal resin. The purification leader sequence can then be subsequently removed by treatment with enterokinase to provide the purified SIP protein (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. SIP Polypeptides

The present invention also makes available isolated and/or purified forms of the subject SIP polypeptides, which are isolated from, or otherwise substantially free of other intracellular proteins, especially ubiquitin conjugating enzymes, e.g. E2 enzymes, which might normally be associated with the SIP protein. The term "substantially free of other cellular proteins" (also referred to herein as "contaminating proteins") is defined as encompassing, for example, SIP preparations comprising less than 20% (by dry weight) contaminating protein, and preferably comprises less than 5% contaminating protein. Functional forms of the SIP polypeptide can be prepared, for the first time, as purified preparations by using a cloned gene as described herein. By "purified", it is meant, when referring to a polypeptide, that the indicated molecule is present in the substantial absence of other biological macromolecules, such as other proteins (contaminating proteins). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

The subject polypeptides can also be provided in pharmaceutically acceptable carriers for formulated for a variety of modes of administration, including systemic and topical or localized administration. Techniques and formulations generally may be found in *Remmington's Pharmaceutical Sciences*, Meade Publishing Co., Easton, Pa. In an exemplary embodiment, the SIP polypeptide is provided for transmucosal or transdermal delivery. For such administration, penetrants appropriate to the barrier to be permeated are used in the formulation with the polypeptide. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

Another aspect of the invention relates to polypeptides derived from the full-length SIP protein. Isolated peptidyl portions of the subject SIP protein can be obtained by screening polypeptides recombinantly produced from the corresponding fragment of the nucleic acid encoding such polypeptides. In addition, fragments can be chemically synthesized using techniques known in the art such as conventional Merrifield solid phase f-Moc or t-Boc chemistry. For example, SIP protein can be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of, for example, p27 degradation, such as by microinjection assays. In an illustrative embodiment, peptidyl portions of a SIP protein can tested for cdc34-binding activity, as well as inhibitory ability, by expression as, for example, thioredoxin fusion proteins, each of which contains a discrete fragment of the SIP protein (see, for example, U.S. Pat. Nos. 5,270,181 and 5,292,646; and PCT publication WO94/02502).

It is also possible to modify the structure of the subject SIP proteins for such purposes as enhancing therapeutic or prophylactic efficacy, or stability (e.g., ex vivo shelf life and resistance to proteolytic degradation in vivo). Such modified polypeptides, when designed to retain at least one activity of the naturally-occurring form of the protein, are considered functional equivalents of the SIP polypeptides described in more detail herein. Such modified polypeptides can be produced, for instance, by amino acid substitution, deletion, or addition.

For instance, it is reasonable to expect, for example, that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry*, 2nd ed., Ed. by L. Stryer, W. H. Freeman and Co., 1981). Whether a change in the amino acid sequence of a polypeptide results in a functional homolog can be readily determined by assessing the ability of the variant polypeptide to produce a response in cells in a fashion similar to the wild-type protein. For instance, such variant forms of a SIP polypeptide can be assessed, e.g., for their ability to bind to another polypeptide, e.g., cdc34. Polypeptides in which more than one replacement has taken place can readily be tested in the same manner.

This invention further contemplates a method of generating sets of combinatorial mutants of the subject SIP proteins, as well as truncation mutants, and is especially useful for identifying potential variant sequences (e.g. homologs) that are functional in binding to a regulatory protein, e.g., p27. The purpose of screening such combinatorial libraries is to generate, for example, SIP homologs which can act as either agonists or antagonist, or alternatively, which possess novel activities all together. Combinatorially-derived homologs can be generated which have a selective potency relative to a naturally occurring SIP protein. Such proteins, when expressed from recombinant DNA constructs, can be used in gene therapy protocols.

Likewise, mutagenesis can give rise to homologs which have intracellular half-lives dramatically different than the corresponding wild-type protein. For example, the altered protein can be rendered either more stable or less stable to proteolytic degradation or other cellular process which result in destruction of, or otherwise inactivation of the SIP protein. Such homologs, and the genes which encode them, can be utilized to alter SIP expression by modulating the half-life of the protein. For instance, a short half-life can give rise to more transient biological effects and, when part of an inducible expression system, can allow tighter control of recombinant SIP protein levels within the cell. As above, such proteins, and particularly their recombinant nucleic acid constructs, can be used in gene therapy protocols.

In similar fashion, SIP homologs can be generated by the present combinatorial approach to act as antagonists, in that they are able to interfere with the ability of the corresponding wild-type protein to regulate cell ubiquitination.

In a representative embodiment of this method, the amino acid sequences for a population of SIP protein homologs are aligned, preferably to promote the highest homology possible. Such a population of variants can include, for example, homologs from one or more species, or homologs from the same species but which differ due to mutation. Amino acids which appear at each position of the aligned sequences are selected to create a degenerate set of combinatorial sequences. In a preferred embodiment, the combinatorial library is produced by way of a degenerate library of genes encoding a library of polypeptides which each include at least a portion of potential SIP protein sequences. For instance, a mixture of synthetic oligonucleotides can be enzymatically ligated into gene sequences such that the degenerate set of potential SIP nucleotide sequences are expressible as individual polypeptides, or alternatively, as a set of larger fusion proteins (e.g. for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential SIP sequences. The synthesis of degenerate oligonucleotides is well known in the art (see for example, Narang, S A (1983) *Tetrahedron* 39:3; Itakura et al., (1981) *Recombinant DNA, Proc.* 3rd Cleveland Sympos. Macromolecules, ed. A G Walton, Amsterdam: Elsevier pp273–289; Itakura et al., (1984) *Annu. Rev. Biochem.* 53:323; Itakura et al., (1984) *Science* 198:1056; Ike et al., (1983) *Nucleic Acid Res.* 11:477). Such techniques have been employed in the directed evolution of other proteins (see, for example, Scott et al., (1990) *Science* 249:386–390; Roberts et al., (1992) *PNAS USA* 89:2429–2433; Devlin et al., (1990) *Science* 249: 404–406; Cwirla et al., (1990) *PNAS USA* 87: 6378–6382; as well as U.S. Pat. Nos: 5,223,409, 5,198,346, and 5,096,815).

Alternatively, other forms of mutagenesis can be utilized to generate a combinatorial library. For example, SIP homologs (both agonist and antagonist forms) can be generated and isolated from a library by screening using, for example, alanine scanning mutagenesis and the like (Ruf et al., (1994) *Biochemistry* 33:1565–1572; Wang et al., (1994) *J. Biol. Chem.* 269:3095–3099; Balint et al., (1993) *Gene* 137:109–118; Grodberg et al., (1993) *Eur. J Biochem.* 218:597–601; Nagashima et al., (1993) *J. Biol. Chem.* 268:2888–2892; Lowman et al., (1991) *Biochemistry* 30:10832–10838; and Cunningham et al., (1989) *Science* 244:1081–1085), by linker scanning mutagenesis (Gustin et al., (1993) *Virology* 193:653–660; Brown et al., (1992) *Mol. Cell Biol.* 12:2644–2652; McKnight et al., (1982) *Science* 232:316); by saturation mutagenesis (Meyers et al., (1986) *Science* 232:613); by PCR mutagenesis (Leung et al., (1989) *Method Cell Mol Biol* 1:11–19); or by random mutagenesis (Miller et al., (1992) A Short Course in Bacterial Genetics, CSHL Press, Cold Spring Harbor, N.Y.; and Greener et al., (1994) *Strategies in Mol Biol* 7:32–34). Linker scanning matagenesis, particularly in a combinatorial setting, is on attractive method for identifying truncated (bioactive) forms of the SIP proteins.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of SIP homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In an illustrative embodiment of a screening assay, candidate SIP combinatorial gene products, are displayed on the surface of a cell, and the ability of particular cells or viral particles to bind p27, cdc4, cdc53, skp1, or other binding partners via this gene product is detected in a "panning assay". For instance, the SIP gene library can be cloned into the gene for a surface membrane protein of a bacterial cell (Ladner et al., WO 88/06630; Fuchs et al., (1991) Bio/Technology 9:1370–1371; and Goward et al., (1992) TIBS 18:136–140), and the resulting fusion protein detected by panning, e.g. using a fluorescently labeled molecule which binds the SIP protein, e.g. FITC-p27, to score for potentially functional homologs. Cells can be visually inspected and separated under a fluorescence microscope, or, where the morphology of the cell permits, separated by a fluorescence-activated cell sorter. While the preceding description is directed to embodiments exploiting the interaction between a SIP polypeptide and another polypeptide, it will be understood that similar embodiments can be generated using, for example, a SIP polypeptide displayed on the surface of a cell and examining the ability of those SIP-expressing cells to bind other binding partners of the SIP protein.

In similar fashion, the gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical E. coli filamentous phages M13, fd, and f1 are most often used in phage display libraries, as either of the phage gIII or gVIII coat proteins can be used to generate fusion proteins without disrupting the ultimate packaging of the viral particle (Ladner et al., PCT publication WO 90/02909; Garrard et al., PCT publication WO 92/09690; Marks et al., (1992) J. Biol. Chem. 267:16007–16010; Griffiths et al., (1993) EMBO J 12:725–734; Clackson et al., (1991) Nature 352:624–628; and Barbas et al., (1992) PNAS USA 89:4457–4461).

The invention also provides for reduction of the subject SIP proteins to generate mimetics, e.g. peptide or non-peptide agents, which are able to mimic binding of the authentic protein to another cellular partner. Such mutagenic techniques as described above, as well as the thioredoxin system, are also particularly useful for mapping the determinants of a SIP protein which participate in protein-protein interactions involved in, for example, binding of the subject proteins to each other. To illustrate, the critical residues of a SIP protein which are involved in molecular recognition of a substrate protein can be determined and used to generate SIP-derived peptidomimetics which bind to the substrate protein, and by inhibiting SIP binding, act to prevent its ubiquitination. By employing, for example, scanning mutagenesis to map the amino acid residues of a SIP protein which are involved in binding p27, peptidomimetic compounds can be generated which mimic those residues in binding to p27. For instance, non-hydrolyzable peptide analogs of such residues can be generated using benzodiazepine (e.g., see Freidinger et al., in Peptides: Chemistry and Biology, G. R. Marshall ed., ESCOM Publisher: Leiden, Netherlands, 1988), azepine (e.g., see Huffman et al., in Peptides: Chemistry and Biology, G. R. Marshall ed., ESCOM Publisher: Leiden, Netherlands, 1988), substituted gama lactam rings (Garvey et al., in Peptides: Chemistry and Biology, G. R. Marshall ed., ESCOM Publisher: Leiden, Netherlands, 1988), keto-methylene pseudopeptides (Ewenson et al., (1986) J. Med. Chem. 29:295; and Ewenson et al., in Peptides: Structure and Function (Proceedings of the 9th American Peptide Symposium) Pierce Chemical Co. Rockland, Ill., 1985), β-turn dipeptide cores (Nagai et al., (1985) Tetrahedron Lett 26:647; and Sato et al., (1986) J Chem Soc Perkin Trans 1:1231), and β-aminoalcohols (Gordon et al., (1985) Biochem Biophys Res Commun 126:419; and Dann et al., (1986) Biochem Biophys Res Commun 134:71).

5. Antibodies to SIP Polypeptides

Another aspect of the invention pertains to an antibody specifically reactive with a SIP protein. For example, by using peptides based on the sequence of the subject vertebrate SIP protein, such as cdc4 antisera or cdc4 monoclonal antibodies, can be made using standard methods. A mammal such as a mouse, a hamster or rabbit can be immunized with an immunogenic form of the peptide (e.g., an antigenic fragment which is capable of eliciting an antibody response). Techniques for conferring immunogenicity on a protein or peptide include conjugation to carriers or other techniques well known in the art. For instance, a peptidyl portion of the protein represented by SEQ ID NO: 2 or 4 can be administered in the presence of adjuvant. The progress of immunization can be monitored by detection of antibody titers in plasma or serum. Standard ELISA or other immunoassays can be used with the immunogen as antigen to assess the levels of antibodies.

Following immunization, anti-SIP antisera can be obtained and, if desired, polyclonal anti-SIP antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) Nature, 256: 495–497), as the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with the SIP proteins and the monoclonal antibodies isolated.

The term antibody as used herein is intended to include fragments thereof which are also specifically reactive with an vertebrate, e.g., mammalia SIP protein. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules, as well as single chain (scFv) antibodies.

Particularly preferred antibodies specific for SIP polypeptides include trimeric antibodies and humanized antibodies, which can be prepared as described, e.g., in U.S. Pat. No. 5,585,089. Also within the scope of the invention are single chain antibodies. All of these modified forms of antibodies as well as fragments of antibodies are intended to be included in the term "antibody" and are included in the broader term "SIP binding protein".

Both monoclonal and polyclonal antibodies (Ab) directed against the subject SIP protein, and antibody fragments such as Fab' and F(ab')$_2$, can be used to selectively block the action of individual SIP proteins and thereby regulate the cell-cycle, cell proliferation, differentiation and/or survival.

In one embodiment, anti-SIP antibodies are used in the immunological screening of cDNA libraries constructed in expression vectors, such as λgt11, λgt18–23, λZAP, and λORF8. Messenger libraries of this type, having coding sequences inserted in the correct reading frame and orientation, can produce fusion proteins. For instance. λgt11 will produce fusion proteins whose amino termini consist of β-galactosidase amino acid sequences and whose carboxy termini consist of a foreign polypeptide. Antigenic epitopes of a SIP protein, such as proteins antigenically related to the SIP protein of SEQ ID NO: 2 or of SEQ ID NO: 4 can then be detected with antibodies, as, for example, reacting nitrocellulose filters lifted from infected plates with an anti-SIP antibody. Phage, scored by this assay, can then be isolated from the infected plate. Thus, SIP homologs can be detected and cloned from other sources.

6. Transgenic Animals

Still another aspect of the invention features transgenic non-human animals which express a heterologous SIP gene of the present invention, or which have had one or more genomic SIP gene(s) disrupted in at least one of the tissue or cell-types of the animal. For instance, transgenic mice that are disrupted at their SIP gene locus can be generated, e.g., by homologous recombination.

In another aspect, the invention features an animal model for developmental diseases, which has an SIP allele which is misexpressed. For example, a mouse can be bred which has an SIP allele deleted, or in which all or part of one or more SIP exons are deleted. Such a mouse model can then be used to study disorders arising from misexpression of the SIP gene.

Accordingly, the present invention concerns transgenic animals which are comprised of cells (of that animal) which contain a transgene of the present invention and which preferably (though optionally) express an exogenous SIP protein in one or more cells in the animal. The SIP transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of the subject protein can be essential for many forms of lineage analysis and can additionally provide a means to assess the effects of, for example, modulation of p27 protein levels, and thus of cell cycle progression which might grossly alter development in small patches of tissue within an otherwise normal embryo. Toward this end, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject SIP polypeptides. For example, excision of a target sequence which interferes with the expression of a recombinant SIP gene can be designed to activate expression of that gene. This interference with expression of the protein can result from a variety of mechanisms, such as spatial separation of the SIP gene from the promoter element or an internal stop codon. Moreover, the transgene can be made wherein the coding sequence of the gene is flanked recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the cre/loxP recombinase system of bacteriophage P1 (Lakso et al., (1992) *PNAS USA* 89:6232–6236; Orban et al., (1992) *PNAS USA* 89:6861–6865) or the FLP recombinase system of *Saccharomyces cerevisiae* (O'Gorman et al., (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al., (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of the SIP gene can be regulated via regulation of recombinase expression.

Use of the cre/loxP recombinase system to regulate expression of a recombinant SIP protein requires the construction of a transgenic animal containing transgenes encoding both the Cre recombinase and the subject protein. Animals containing both the Cre recombinase and the recombinant SIP genes can be provided through the construction of "double" transgenic animals. A convenient method for providing such animals is to mate two transgenic animals each containing a transgene, e.g., the SIP gene and recombinase gene.

One advantage derived from initially constructing transgenic animals containing an SIP transgene in a recombinase-mediated expressible format derives from the likelihood that the subject protein may be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues. Thus, the creation of a founder population in which, for example, an antagonistic SIP transgene is silent will allow the study of progeny from that founder in which disruption of cell-cycle regulation in a particular tissue or at developmental stages would result in, for example, a lethal phenotype.

Similar conditional transgenes can be provided using prokaryotic promoter sequences which require prokaryotic proteins to be simultaneous expressed in order to facilitate expression of the transgene. Exemplary promoters and the corresponding transactivating prokaryotic proteins are given in U.S. Pat. No. 4,833,080. Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, the SIP transgene could remain silent into adulthood until "turned on" by the introduction of the transactivator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al., (1985) *PNAS USA* 82:4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS USA* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al., (1985) *PNAS USA* 82:6927–6931; Van der Putten et al., (1985) *PNAS USA* 82:6148–6152). Transfection is easily and efficiently obtained by culturing the blastomeres on a monolayer of virus-producing cells (Van der Putten, supra; Stewart et al., (1987) *EMBO J.* 6:383–388). Alternatively, infection can be performed at a later stage. Virus or virus-producing cells can be injected into the blastocoele (Jahner et al., (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al., (1982) supra).

A third type of target cell for transgene introduction is the embryonal stem cell (ES). ES cells are obtained from pre-implantation embryos cultured in vitro and fused with embryos (Evans et al., (1981) *Nature* 292:154–156; Bradley et al., (1984) *Nature* 309:255–258; Gossler et al., (1986) *PNAS USA* 83: 9065–9069; and Robertson et al., (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

Methods of making knock-out or disruption transgenic animals are also generally known. See, for example, *Manipulating the Mouse Embryo*, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of an SIP gene can be controlled as above.

7. Detection of the subject SIP genes and gene products

Antibodies which are specifically immunoreactive with a SIP protein of the present invention can also be used in immunohistochemical staining of tissue samples in order to evaluate the abundance and pattern of expression of the protein. Anti-SIP antibodies can be used diagnostically in immuno-precipitation and immuno-blotting to detect and evaluate levels of one or more SIP proteins in tissue or cells isolated from a bodily fluid as part of a clinical testing procedure. Diagnostic assays using anti-SIP antibodies, can include, for example, immunoassays designed to aid in early diagnosis of a neoplastic or hyperplastic disorder, e.g. the presence of cancerous cells in the sample, e.g. to detect cells in which alterations in expression levels of SIP genes has occurred relative to normal cells.

In addition, nucleotide probes can be generated from the cloned sequence of the subject SIP proteins which allow for histological screening of intact tissue and tissue samples for the presence of a SIP protein encoding nucleic acids. Similar to the diagnostic uses of anti-SIP protein antibodies, the use of probes directed to SIP protein encoding mRNAs, or to genomic SIP gene sequences, can be used for both predictive and therapeutic evaluation of allelic mutations which might be manifest in, for example, neoplastic or hyperplastic disorders (e.g. unwanted cell growth) or unwanted differentiation events.

Used in conjunction with anti-SIP protein antibody immunoassays, the nucleotide probes can help facilitate the determination of the molecular basis for a developmental disorder which may involve some abnormality associated with expression (or lack thereof) of a SIP protein. For instance, variation in SIP protein synthesis can be differentiated from a mutation in the coding sequence.

In one embodiment, the present method provides a method for determining if a subject is at risk for a disorder characterized by protein degradation, aberrant cell proliferation and/or differentiation. In preferred embodiments, method can be generally characterized as comprising detecting, in a sample of cells from a vertebrate subject (preferably a human or other mammalian subject), the presence or absence of a genetic lesion characterized by at least one of (i) an alteration affecting the integrity of a cdc4 gene; or (ii) the misexpression of the SIP gene. To illustrate, such genetic lesions can be detected by ascertaining the existence of at least one of (i) a deletion of one or more nucleotides from an SIP gene, (ii) an addition of one or more nucleotides to an SIP gene, (iii) a substitution of one or more nucleotides of an SIP gene, (iv) a gross chromosomal rearrangement of an SIP gene, (v) a gross alteration in the level of a messenger RNA transcript of an SIP gene, (vii) aberrant modification of an SIP gene, such as of the methylation pattern of the genomic DNA, (vii) the presence of a non-wild type splicing pattern of a messenger RNA transcript of an SIP gene, (viii) a non-wild type level of a SIP protein, and (ix) inappropriate post-translational modification of a SIP protein. As set out below, the present invention provides a large number of assay techniques for detecting lesions in an SIP gene, and importantly, provides the ability to discern between different molecular causes underlying SIP dependent aberrant cell growth, proliferation and/or differentiation.

In an exemplary embodiment, there is provided a nucleic acid composition comprising a (purified) oligonucleotide probe including a region of nucleotide sequence which is capable of hybridizing to a sense or antisense sequence of an SIP gene, such as represented by any of SEQ ID NOs: 1 or 3, or naturally occurring mutants thereof, or 5' or 3' flanking sequences or intronic sequences naturally associated with the subject SIP genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., (1988) *Science* 241:1077–1080; and Nakazawa et al., (1944) *PNAS USA* 91:360–364), the later of which can be particularly useful for detecting point mutations in the SIP gene. In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to an SIP gene under conditions such that hybridization and amplification of the SIP gene (if present) occurs, and (iv) detecting the presence or absence of an amplification product, or detecting the size of the amplification product and comparing the length to a control sample.

In yet another exemplary embodiment, aberrant methylation patterns of an SIP gene can be detected by digesting genomic DNA from a patient sample with one or more restriction endonucleases that are sensitive to methylation and for which recognition sites exist in the SIP gene (including in the flanking and intronic sequences). See, for example, Buiting et al., (1994) *Human Mol Genet* 3:893–895. Digested DNA is separated by gel electrophoresis, and hybridized with probes derived from, for example, genomic or cDNA sequences. The methylation status of the SIP gene can be determined by comparison of the restriction pattern generated from the sample DNA with that for a standard of known methylation.

In still another embodiment, a diagnostic assay is provided which detects the ability of an SIP gene product, e.g., isolated from a biopsied cell, to bind to other cellular proteins. For instance, it will be desirable to detect SIP mutants which bind with higher or lower binding affinity for another SIP protein, for a ubiquitin conjugating enzyme, or for a substrate protein. Such mutants may arise, for example, from fine mutations, e.g., point mutants, which may be impractical to detect by the diagnostic DNA sequencing techniques or by the immunoassays described above. The present invention accordingly further contemplates diagnostic screening assays which generally comprise cloning one or more SIP genes from the sample cells, and expressing the cloned genes under conditions which permit detection of an interaction between that recombinant gene product and a substrate protein, e.g., another SIP protein. As will be apparent from the description of the various drug screening assays set forth below, a wide variety of techniques can be used to determine the ability of a SIP protein to bind to other cellular components.

The CKI proteins have been suggested as potential anti-oncogenes since their function is often missing in transformed cells. For instance, the Ink4 genes p15 and p16 have been found mutated, deleted or inactivated by methylation in a large number of human malignancies. The CIP1 gene p21 is transcriptionally induced by the tumor suppressor p53, whose function is lacking in about 50% of human tumors. It has been found that in p53 minus cells, p21 is poorly expressed and is not associated with CDKs. In contrast, the p27 gene analyzed by Southern blot and PCR-SSCP in a large number of human cancers and human cell lines showed no structural alterations of point mutations (Kawamat et al. (1995) *Cancer Res* 55:2266; Ponce-Castaneda et al. (1995) *Cancer Res* 55:1211; and Pietenpol et al. (1995) *Cancer Res* 55:1206).

Recently it has been demonstrated by immunohistochemistry that p27 protein levels are reduced in primary breast cancers and that this is associated with tumor progression in both in situ and invasive lesions. Moreover, p27 was determined to be an independent prognostic marker in small invasive breast carcinomas, being correlated with recurrence and mortality rates. See, for example, Tan et al. (1997) *Cancer Res* 57:1259; Porter et al. (1997) *Nature Medicine* 3:222; and Catzavelos et al. (1997) *Nature Medicine* 3:227. Thus, another aspect of the instant invention is based on the discovery that the level of cdc4 activity, resulting from expression, stability and/or activation, can be inversely correlated to the level of p27 protein, and thus correlated with progression of a hyperproliferative disorder. The level of cdc4 transcript, protein, and/or ligase activity can be used predictively to evaluate whether a sample of cells contains cells which are, or are predisposed towards becoming, transformed cells. In general, the subject method can be characterized as including a step of detecting, in a sample of cells from the subject, the level of a cdc4 protein (or other SIP ligase).

For example, the subject method can comprise the steps of: (i) ascertaining the level of a cdc4 protein, cdc4 transcript and/or cdc4 ligase activity in a sample of cells from the patient; and (ii) evaluating, from such levels in the sample cells compared to normal cells, the aggressiveness and/or prospective rate of recurrence of a disorder marked by aberrant hyperproliferation. As will be understood by those skilled in the art, the method of the present invention can be carried out using any of a large number of assay techniques for detecting the cdc4 protein and/or its ligase activity, and importantly, provides the ability to discern between different molecular causes underlying aberrant cell growth, proliferation and/or differentiation.

Moreover, the subject method can be used to assess the phenotype of cells which are known to be transformed, the phenotyping results being useful in planning a particular therapeutic regimen. For instance, as the art suggests, absence or low p27 protein expression is a poweful negative diagnostic and prognostic marker for a variety of cancerous diseases. The loss of p27 protein can be utilized in decisions regarding, e.g., the use of more aggressive therapies. The upregulation of cdc4 activity can be used in similar fashion.

Prognosis in clinical cancer is an area of great concern and interest. It is important to know the aggressiveness of the malignant cells and the likelihood of tumor recurrence in order to plan the most effective therapy. Breast cancer, for example, is managed by several alternative strategies. In some cases local-regional and systemic radiation therapy is utilized while in other cases mastectomy and chemotherapy or mastectomy and radiation therapy are employed. As known in the art, treatment decisions for individual breast cancer patients can be based on, for example, the number of axillary lymph nodes involved with disease, estrogen receptor and progesterone receptor status, the size of the primary tumor, and stage of disease at diagnosis. It has also been reported that DNA aneuploidy and proliferative rate (percent S-phase) can help in predicting the course of disease (Dressler et al., (1988) Cancer 61:420; and Clark et al., (1989) N. Engl. J. Med. 320:627). The subject method provides a means for accurately predicting the course of disease for breast cancer patients. The ability to detect destabilization of the p27 protein by overexpression or overactivation of cdc4 can facilitate separation of patients with good prognosis, e.g., who will need little to no further therapy, from those more likely to recur who might benefit from more intensive treatments. This index can be combined with other prognostic methods.

This is particularly true in the case of breast cancer which has not progressed to the axillary lymph nodes ("node negative"). There is now evidence in prospective randomized clinical trials that adjuvant endocrine therapy and adjuvant chemotherapy beginning immediately after surgical removal of the primary breast tumor can be of benefit in some of these node-negative patients. This has led to recommendations in the art that most if not all node-negative breast cancer patients should be considered for some form of adjuvant therapy. But since the majority (approximately equal to 70%) of these patients enjoy long-term survival following surgery and/or radiotherapy without further treatment, it may be inappropriate to recommend adjuvant therapy for all of these patients. The subject method can be used to distinguish those node-negative patients on the basis of significantly elevated or reduced risk of mortality, and suggests that this index may be useful in determining which patients would benefit from, e.g., continued and/or more aggressive therapy (such as adjuvant therapies).

It will also be appreciated that the subject method provides a procedure for predicting tumor recurrence in cancer patients in general, once the primary tumor is detected. The present invention is a significant step in the ability to predict with some confidence the likelihood of cancer recurrence. It is clear from the extensive studies on the p27 protein that it has an important physiological role, and the recent publications have been able to relate its cellular levels or presence to clinical manifestations of dysfunction. Now the survival risk to cancer patients can be better assessed and aggressive therapies applied as indicated to those in high risk groups.

The term "prognosis" is art recognized and, as set out above, concerns the likelihood that an individual may suffer occurrence, relapse or distant relapse of cancerous disease. Relapse is the recurrence of tumor growth due to propagation of tumor cells remaining in the host after treatment, new tumor cell development, or the like. Distant relapse concerns tumor dissemination such that tumor growth occurs at a site distant from the site of the original tumor. Of additional interest in the case of disease relapse is the length of the relapse-free survival time. Relapse-free survival time is the period between either surgical removal of the tumor or the suppression or mitigation of tumor growth and the recurrence of cancerous disease. Prognosis may be affected by various criteria such as histological type, tumor grade, tumor size, ploidy, and expression of certain hormone receptors such as estrogen receptor, and, according to the present invention, the level of expression and/or activity of cdc4. These criteria provide some guidance in determining the need for and efficacy of subjecting the patient to various cancer therapies, such as irradiation, adjuvant therapy or surgical procedures such as mastectomy in the case of breast cancer.

To further illustrate the art describes that levels of p27 protein, but not levels of p27 mRNA, are decreased in a variety of different tumor cells. For example, it was found that normal colonic mucosa, and well to moderately differentiated (less agressive) adenocarcinomas showed a strong p27 nuclear signal. In contrast, most of the poorly differentiated, highly aggressive adenocarcinomas showed a very low percentage of p27 positive cells. Furthermore, a highly significant correlation between the presence of p27 and survival of the patient was found. No correlation between the mitotic index of a particular tumor and p27 expression was found. Likewise, evaluation of biopsied tissue of a series of patients illustrates that the level of p27 protein provides a diagnostic and prognostic marker for breast cancers.

The art further describes an immunohistochemical analysis of p27 protein levels in breast ductal carcinomas, and the findings that low levels of p27 (p=0.01) were strongly predictive of increased mortality, both before and after adjustment for other clinical and pathological characteristics. Distant relapse-free survival, which is defined as survival without formation of tumors distant from the original site, is significantly inversely correlated with the combined analysis of the percent of p27 minus tumor cells. This enabled us to subdivide women with localized, node-negative disease into groups with either significantly elevated or reduced risk of mortality, and suggested that this index may be useful in determining which patients would benefit from more aggressive therapy.

The subject method is applicable to the diagnosis/prognosis of such breast cancer types as ductal, mucinous, lobular and the like. The cancer may be detected at any stage of tumor development, including hyperplasia, in situ and the like. The subject invention finds particular application for diagnosis where the patient carries an axillary lymph-node negative, ductal carcinoma of the breast.

The subject method can also be used to augment the detection and/or prognosis of such solid tumors as, for example, carcinomas (particularly epithelial-derived carcinomas) of such tissues as ovaries, lung, intestinal, pancreas, prostate, testis, liver, skin, stomach, renal, cervical, colorectal, and head and neck; melanomas; and sarcomas such as Kaposi's sarcoma and rhabdomyosarcoma. In preferred embodiments, the subject method is used to assess a malignant or pre-malignant epithelial carcinoma.

The diagnostic methods of the subject invention may also be employed as follow-up to treatment, e.g., quantitation of the level of cdc4 protein or its ligase activity may be indicative of the effectiveness of current or previously employed cancer therapies as well as the effect of these therapies upon patient prognosis.

Accordingly, the present invention makes available diagnostic assays and reagents for detecting upregulation of cdc4 protein from a cell in order to aid in the diagnosis and phenotyping of proliferative disorders arising from, for example, tumorigenic transformation of cells, or other hyperplastic or neoplastic transformation processes, as well as differentiative disorders, such as degeneration of tissue, e.g. neurodegeneration.

8. Gene Therapy

The invention provides methods for modulating ubiquitination and subsequent degradation of substrate proteins, including cell cycle regulatory proteins. Accordingly, the invention provides methods for modulating cell proliferation, differentiation and/or survival, which can be used, for e.g. to treat diseases or conditions associated with an aberrant protein degradation, cell proliferation, differentiation and/or survival. According to the methods of the invention, an SIP therapeutic is administered to a subject having a disease associated with aberrant protein degradation, cell proliferation, differentiation and/or cell survival.

There are a wide variety of pathological cell proliferative conditions for which the SIP gene constructs, SIP mimetics and SIP antagonists, of the present invention can provide therapeutic benefits, with the general strategy being the modulation of anomalous cell proliferation. For instance, the gene constructs of the present invention can be used as a part of a gene therapy protocol, such as to reconstitute the function of a cdc4 protein, e.g. in a cell in which the protein is misexpressed or in which signal transduction pathways upstream of a SIP protein are dysfunctional, or to inhibit the function of the wild-type protein, e.g. by delivery of a dominant negative mutant.

To illustrate, cell types which exhibit pathological or abnormal growth presumably dependent at least in part on a function (or dysfunction) of a SIP protein include various cancers and leukemias, psoriasis, bone diseases, fibroproliferative disorders such as involving connective tissues, atherosclerosis and other smooth muscle proliferative disorders, as well as chronic inflammation. In addition to proliferative disorders, the treatment of differentiative disorders which result from either de-differentiation of tissue due to aberrant reentry into mitosis, or unwanted differentiation due to a failure of a regulatory protein such as p27, or a G1 phase cyclin.

It will also be apparent that, by transient use of gene therapy constructs of the subject SIP proteins (e.g. agonist and antagonist forms) or antisense nucleic acids, in vivo reformation of tissue can be accomplished, e.g. in the development and maintenance of organs. By controlling the proliferative and differentiative potential for different cells, the subject gene constructs can be used to reform injured tissue, or to improve grafting and morphology of transplanted tissue. For instance, SIP agonists and antagonists can be employed therapeutically to regulate organs after physical, chemical or pathological insult. For example, gene therapy can be utilized in liver repair subsequent to a partial hepatectomy, or to promote regeneration of lung tissue in the treatment of emphysema.

In one aspect of the invention, expression constructs of the subject SIP proteins, or for generating antisense molecules, may be administered in any biologically effective carrier, e.g. any formulation or composition capable of effectively transfecting cells in vivo with a recombinant SIP gene. Approaches include insertion of the subject gene in viral vectors including recombinant retroviruses, adenovirus, adeno-associated virus, and herpes simplex virus-1, or recombinant bacterial or eukaryotic plasmids. Viral vectors can be used to transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid encoding one of the subject proteins into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding a SIP polypeptide, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al., (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis et al., (1985) *Science* 230:1395–1398; Danos and Mulligan, (1988) *PNAS USA* 85:6460–6464; Wilson et al., (1988) *PNAS USA* 85:3014–3018; Armentano et al., (1990) *PNAS USA* 87:6141–6145; Huber et al., (1991) *PNAS USA* 88:8039–8043; Ferry et al., (1991) *PNAS USA* 88:8377–8381; Chowdhury et al., (1991) *Science* 254:1802–1805; van Beusechem et al., (1992) *PNAS USA* 89:7640–7644; Kay et al., (1992) *Human Gene Therapy* 3:641–647; Dai et al., (1992) *PNAS USA* 89:10892–10895; Hwu et al., (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., (1989) *PNAS USA* 86:9079–9083; Julan et al., (1992) *J. Gen Virol* 73:3251–3255; and Goud et al., (1983) *Virology* 163:251–254); or coupling cell surface ligands to the viral env proteins (Neda et al., (1991) *J. Biol. Chem.* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Another viral gene delivery system useful in the present invention utilizes adenovirus-derived vectors. The genome of an adenovirus can be manipulated such that it encodes a gene product of interest, but is inactivate in terms of its ability to replicate in a normal lytic viral life cycle (see, for example, Berkner et al., (1988) *BioTechniques* 6:616; Rosenfeld et al., (1991) *Science* 252:431–434; and Rosenfeld et al., (1992) *Cell* 68:143–155). Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al., (1992) cited supra), endothelial cells (Lemarchand et al., (1992) *PNAS USA* 89:6482–6486), hepatocytes (Herz and Gerard, (1993) *PNAS USA* 90:2812–2816) and muscle cells (Quantin et al., (1992) *PNAS USA* 89:2581–2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al., (1979) *Cell* 16:683; Berkner et al., supra; and Graham et al., in *Methods in Molecular Biology*, E. J. Murray, Ed. (Humana, Clifton, N.J., 1991) vol. 7. pp. 109–127). Expression of the inserted SIP gene can be under control of, for example, the E1A promoter, the major late promoter (MLP) and associated leader sequences, the viral E3 promoter, or exogenously added promoter sequences.

Yet another viral vector system useful for delivery of the subject SIP genes is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., *Curr. Topics in Micro. and Immunol.* (1992) 158:97–129). It is also one of the few viruses that may integrate its DNA into non-dividing cells, and exhibits a high frequency of stable integration (see for example Flotte et al., (1992) *Am. J. Respir. Cell. Mol. Biol.* 7:349–356; Samulski et al., (1989) *J. Virol.* 63:3822–3828; and McLaughlin et al., (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al., (1985) *Mol. Cell. Biol.* 5:3251–3260 can be used to introduce DNA into cells. A variety of nucleic acids have been introduced into different cell types using AAV vectors (see for example Hermonat et al., (1984) *PNAS USA* 81:6466–6470; Tratschin et al., (1985) *Mol. Cell. Biol.* 4:2072–2081; Wondisford et al., (1988) *Mol. Endocrinol.* 2:32–39; Tratschin et al., (1984) *J. Virol.* 51:611–619; and Flotte et al., (1993) *J. Biol. Chem.* 268:3781–3790).

Other viral vector systems that may have application in gene therapy have been derived from herpes virus, vaccinia virus, and several RNA viruses. In particular, herpes virus vectors may provide a unique strategy for persistence of the recombinant SIP gene in cells of the central nervous system and ocular tissue (Pepose et al., (1994) *Invest Ophthalmol Vis Sci* 35:2662–2666)

In addition to viral transfer methods, such as those illustrated above, non-viral methods can also be employed to cause expression of a SIP protein in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject SIP gene by the targeted cell. Exemplary gene delivery systems of this type include liposomal derived systems, poly-lysine conjugates, and artificial viral envelopes.

In a representative embodiment, a gene encoding a SIP polypeptide can be entrapped in liposomes bearing positive charges on their surface (e.g., lipofectins) and (optionally) which are tagged with antibodies against cell surface antigens of the target tissue (Mizuno et al., (1992) *No Shinkei Geka* 20:547–551; PCT publication WO91/06309; Japanese patent application 1047381; and European patent publication EP-A-43075). For example, lipofection of neuroglioma cells can be carried out using liposomes tagged with monoclonal antibodies against glioma-associated antigen (Mizuno et al., (1992) *Neurol. Med. Chir.* 32:873–876).

In yet another illustrative embodiment, the gene delivery system comprises an antibody or cell surface ligand which is cross-linked with a gene binding agent such as poly-lysine (see, for example, PCT publications WO93/04701, WO92/

22635, WO92/20316, WO92/19749, and WO92/06180). For example, the subject SIP gene construct can be used to transfect specific cells in vivo using a soluble polynucleotide carrier comprising an antibody conjugated to a polycation, e.g. poly-lysine (see U.S. Pat. No. 5,166,320). It will also be appreciated that effective delivery of the subject nucleic acid constructs via-mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al., (1993) *Science* 260–926; Wagner et al., (1992) *PNAS USA* 89:7934; and Christiano et al., (1993) *PNAS USA* 90:2122).

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction of the construct in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al., (1994) *PNAS USA* 91: 3054–3057).

9. Drug Screening Assays

The present invention also provides assays for identifying drugs which are either agonists or antagonists of the normal cellular function of the subject SIP proteins, or of the role of those proteins in the pathogenesis of normal or abnormal cellular proliferation and/or differentiation and disorders related thereto, as mediated by, for example, the ubiquitination of p27 or other regulatory proteins by an SIP-dependent process. In one embodiment, the assay evaluates the ability of a compound to modulate binding and/or ubiquitinylation of a p27 (or other cellular or viral substrate) by an SIP ligase. Such modulators can be used, for example, in the treatment of proliferative and/or differentiative disorders, and to modulate apoptosis.

A variety of assay formats will suffice and, in light of the present disclosure, those not expressly described herein will nevertheless be comprehended by one of ordinary skill in the art. Assay formats which approximate the ubiquitination of target polypeptides as mediated by E3 complexes can be generated in many different forms, and include assays based on cell-free systems, e.g. purified proteins or cell lysates, as well as cell-based assays which utilize intact cells. Simple binding assays can also be used to detect agents which, by disrupting the binding of an E2 to a SIP protein or complex, or the binding of a SIP protein or complex to a substrate, can inhibit SIP-dependent ubiquitination. Agents to be tested for their ability to act as SIP inhibitors can be produced, for example, by bacteria, yeast or other organisms (e.g. natural products), produced chemically (e.g. small molecules, including peptidomimetics), or produced recombinantly. In a preferred embodiment, the test agent is a small organic molecule, e.g., other than a peptide or oligonucleotide, having a molecular weight of less than about 2,000 daltons.

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target. Accordingly, potential modifiers, e.g., activators or inhibitors of SIP-dependent ubiquitination of a polypeptide substrate can be detected in a cell-free assay generated by constitution of a functional ubiquitin conjugating system in a cell lysate, such as generated by charging a ubiquitin-depleted reticulocyte lysate (Hershko et al., (1983) *J Biol Chem* 258:8206–8214) with one or more of a ubiquitin-conjugating enzyme, an E1 enzyme, an E2 enzyme, a SIP ligase, ubiquitin, and/or a substrate for SIP-dependent ubiquitination, such as a CDK inhibitor, a cyclin or other cell-cycle regulatory protein. In an alternate format, the assay can be derived as a reconstituted protein mixture which, as described below, offers a number of benefits over lysate-based assays.

For convenience, the subject assays are described below with reference to p27 polypeptides the substrate polypeptide in the reaction mixture. However, the skilled artisan will readily recognize that other substrate polypeptides can be substituted for p27. For example, the substrate polypeptide can be another CDK inhibitor (CKI polypeptide), a cyclin (preferably a G1 phase cyclin), IκB, myc or other cellular or viral protein which is ubiquitinated in a SIP ligase-dependent manner.

In one aspect, the present invention provides assays that can be used to screen for drugs which modulate the conjugation of ubiquitin to p27. For instance, the drug screening assays of the present invention can be designed to detect agents which disrupt binding of a SIP protein (such as cdc4), to p27. In other embodiments, the subject assays will identify inhibitors of the enzymatic activity of the SIP ligase, e.g., which inhibitors prevent transfer of ubiquitin from the ligase to p27, or which inhibit the transfer of ubiquitin from an E2 enzyme, such as UBC2 or UBC3, to a SIP amino acid side chain (e.g., the active site cysteine). In a preferred embodiment, the agent is a mechanism based inhibitor which chemically alters the enzyme, e.g. covalently binds an active site cysteine residue of a SIP ligase, and which is a specific inhibitor of that enzyme, e.g. has an inhibition constant 10-fold, 100-fold, or more preferably, 1000-fold different for other human E3 ligases.

In many embodiments of the subject assay which utilize a ubiquitin-competent system, the level of ubiquitination of a substrate p27 polypeptide brought about by the ubiquitin-conjugating system is measured in the presence and absence of a candidate agent, and a decrease in the level of ubiquitin conjugation is indicative of an inhibitory activity for the candidate agent. As described below, the level of ubiquitination of the p27 polypeptide can be measured by determining the actual concentration of p27:ubiquitin conjugates formed; or inferred by detecting some other quality of the subject p27 polypeptide affected by ubiquitination, including the proteolytic degradation of the protein. A statistically significant decrease in ubiquitination of the p27 polypeptide in the presence of the test compound is indicative of the test compound being an inhibitor of SIP ligase-dependent ubiquitin conjugation of p27.

In preferred in vitro embodiments of the present assay, the ubiquitin-conjugating system comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in conjugation of ubiquitin to a p27 polypeptide, together with the p27 polypeptide, are present in the mixture to at least 50% purity relative to all other proteins in the mixture, and more preferably are present at 90–95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure specific ubiquitination or ubiquitin-mediated degradation of the target p27 polypeptide.

With respect to measuring ubiquitination, the purified protein mixture can substantially lack any proteolytic activity which would degrade the p27 polypeptide and/or components of the ubiquitin conjugating system. For instance, the reconstituted system can be generated to have less than 10% of the proteolytic activity associated with a typical lysate, and preferably no more than 5%, and most preferably less than 2%. Alternatively, the mixture can be generated to include, either from the onset of ubiquitination or from some point after ubiquitin conjugation of the p27 polypeptide, a ubiquitin-dependent proteolytic activity, such as a purified proteosome complex, that is present in the mixture in discrete, measured amounts.

In the subject method, ubiquitin conjugating systems derived from purified proteins can hold a number of significant advantages over cell lysate or wheat germ extract based assays (collectively referred to hereinafter as "lysates"). Unlike the reconstituted protein system, the synthesis and destruction of the p27 polypeptide cannot be readily controlled for in lysate-based assays. Without knowledge of particular kinetic parameters for Ub-independent and Ub-dependent degradation of the p27 polypeptide in the lysate, discerning between the two pathways can be extremely difficult. Measuring these parameters, if at all possible, is further made tedious by the fact that cell lysates tend to be inconsistent from batch to batch, with potentially significant variation between preparations. Evaluation of a potential inhibitor using a lysate system is also complicated in those circumstances where the lysate is charged with mRNA encoding the p27 polypeptide, as such lysates may continue to synthesize the protein during the assay, and will do so at unpredictable rates.

Using similar considerations, knowledge of the concentration of each component of the ubiquitin conjugation pathway can be required for each lysate batch, along with the degradative kinetic data, in order to determine the necessary time course and calculate the sensitivity of experiments performed from one lysate preparation to the next.

Furthermore, the lysate system can be unsatisfactory where the substrate polypeptide itself has a relatively short half-life, especially if due to degradative processes other than the ubiquitin-mediated pathway to which an inhibitor is sought.

In one embodiment, the use of reconstituted protein mixtures allows more careful control of the reaction conditions in the ubiquitin-conjugating system. Moreover, the system can be derived to favor discovery of inhibitors of particular steps of the ubiquitination process. For instance, a reconstituted protein assay can be generated which does not facilitate degradation of the ubiquitinated p27 polypeptide. The level of ubiquitin conjugated p27 polypeptide can easily be measured directly in such as system, both in the presence and absence of a candidate agent, thereby enhancing the ability to detect an inhibitor of SIP-dependent ubiquitination. Alternatively, the Ub-conjugating system can be allowed to develop a steady state level of p27:Ub conjugates in the absence of a proteolytic activity, but then shifted to a degradative system by addition of purified Ub-dependent proteases. Such degradative systems would be amenable to identifying proteosome inhibitors.

The purified protein mixture includes a purified preparation of the p27 polypeptide and SIP proteins under conditions which drive the conjugation of the two molecules. For instance, the mixture can include a ubiquitin-activating enzyme (E1), a ubiquitin-conjugating enzyme (E2) such as UBC2 or UBC3, and a nucleotide triphosphate (e.g. ATP). Alternatively, the E1 enzyme, the ubiquitin, and the nucleotide triphosphate can be substituted in the system with a pre-activated ubiquitin in the form of an E1::Ub or E2::Ub conjugate. Likewise, a pre-activated ubiquitin can instead comprise an SIP::Ub conjugate which can directly transfer the pre-activated ubiquitin to the p27 polypeptide substrate.

Ubiquitination of the target p27 polypeptide via an in vitro ubiquitin-conjugating system, in the presence and absence of a candidate inhibitor, can be accomplished in any vessel suitable for containing the reactants. Examples include microtitre plates, test tubes, and micro-centrifuge tubes. In certain embodiments of the present assay, the in vitro assay system is generated to lack the ability to degrade the ubiquitinated p27 polypeptide. In such an embodiments, a wide range of detection means can be practiced to score for the presence of the ubiquitinated protein.

In one embodiment of the present assay, the products of a non-degradative ubiquitin-conjugating system are separated by gel electrophoresis, and the level of ubiquitinated p27 polypeptide assessed, using standard electrophoresis protocols, by measuring an increase in molecular weight of the p27 polypeptide that corresponds to the addition of one or more ubiquitin chains. For example, one or both of the p27 polypeptide and ubiquitin can be labeled with a radioisotope such as $^{35}S$, $^{14}C$, or $^{3}H$, and the isotopically labeled protein bands quantified by autoradiographic techniques. Standardization of the assay samples can be accomplished, for instance, by adding known quantities of labeled proteins which are not themselves subject to ubiquitination or degradation under the conditions which the assay is performed. Similarly, other means of detecting electrophoretically separated proteins can be employed to quantify the level of ubiquitination of the p27 polypeptide, including immunoblot analysis using antibodies specific for either the p27 polypeptide or ubiquitin, or derivatives thereof. As described below, the antibody can be replaced with another molecule able to bind one of either the p27 polypeptide or ubiquitin. By way of illustration, one embodiment of the present assay comprises the use of biotinylated ubiquitin in the conjugating system. The biotin label is detected in a gel during a subsequent detection step by contacting the electrophoretic products (or a blot thereof) with a streptavidin-conjugated label, such as a streptavidin linked fluorochrome or enzyme, which can be readily detected by conventional techniques. Moreover, where a reconstituted protein mixture is used (rather than a lysate) as the conjugating system, it may be possible to simply detect the p27 polypeptide and ubiquitin conjugates thereof in the gel by standard staining protocols, including coomassie blue and silver staining.

In another embodiment, an immunoassay or similar binding assay, is used to detect and quantify the level of ubiquitinated p27 polypeptide produced in the ubiquitin-conjugating system. Many different immunoassay techniques are amenable for such use and can be employed to detect and quantitate the p27:Ub conjugates. For example, the wells of a microtitre plate (or other suitable solid phase) can be coated with an antibody which specifically binds one of either the p27 polypeptide or ubiquitin. After incubation of the ubiquitin-conjugated system with and without the candidate agent, the products are contacted with the matrix bound antibody, unbound material removed by washing, and ubiquitin conjugates of the p27 polypeptide specifically detected. To illustrate, if an antibody which binds the p27 polypeptide is used to sequester the polypeptide on the matrix, then a detectable anti-ubiquitin antibody can be used to score for the presence of ubiquitinated p27 polypeptide on the matrix.

However, the use of antibodies in these binding assays is merely illustrative of binding molecules in general, and that the antibodies are readily substituted in the assay with any suitable molecule that can specifically detect one of either the p27 polypeptide or the ubiquitin. As described below, a biotin-derivative of ubiquitin can be used, and streptavidin (or avidin) employed to bind the biotinylated ubiquitin. In an illustrative embodiment, wells of a microtitre plate are coated with streptavidin and contacted with the developed ubiquitin-conjugating system under conditions wherein the biotinylated ubiquitin binds to and is sequestered in the wells. Unbound material is washed from the wells, and the level of p27 polypeptide (bound to the matrix via a conjugated ubiquitin moiety) is detected in each well. Alternatively, the microtitre plate wells can be coated with an antibody (or other binding molecule) which binds and sequesters the p27 polypeptide on the solid support, and detection of ubiquitinated conjugates of the matrix-bound p27 polypeptide are subsequently carried out using a detectable streptavidin derivative, such as an alkaline phosphatase/streptavidin complex.

In similar fashion, epitope-tagged ubiquitin, such as myc-ub (see Ellison et al. (1991) *J. Biol. Chem.* 266:21150–21157; ubiquitin which includes a 10-residue sequence encoding a protein of c-myc) can be used in conjunction with antibodies to the epitope tag. A major advantage of using such an epitope-tagged ubiquitin approach for detecting Ub:protein conjugates is the ability of an N-terminal tag sequences to inhibit ubiquitin-mediated proteolysis of the conjugated p27 polypeptide.

Other ubiquitin derivatives include detectable labels which do not interfere greatly with the conjugation of ubiquitin to the p27 polypeptide. Such detectable lables can include fluorescently-labeled (e.g. FITC) or enzymatically-labeled ubiquitin fusion proteins. These derivatives can be produced by chemical cross-linking, or, where the label is a protein, by generation of a fusion protein. Several labeled ubiquitin derivatives are commercially available.

Likewise, other binding molecules can be employed in place of the antibodies that bind the p27 polypeptide. For example, the p27 polypeptide can be generated as a glutathione-S-transferase (GST) fusion protein. As a practical matter, such GST fusion protein can enable easy purification of the p27 polypeptide in the preparation of components of the ubiquitin-conjugating system (see, for example, *Current Protocols in Molecular Biology*, eds. Ausubel et al. (NY: John Wiley & Sons, 1991); Smith et al. (1988) *Gene* 67:31; and Kaelin et al. (1992) Cell 70:351) Moreover, glutathione derivatized matrices (e.g. glutathione-sepharose or glutathione-coated microtitre plates) can be used to sequester free and ubiquitinated forms of the p27 polypeptide from the ubiquitin-conjugating system, and the level of ubiquitin immobilized can be measured as described. Likewise, where the matrix is generated to bind ubiquitin, the level of sequestered GST-p27 polypeptide can be detected using agents which bind to the GST moiety (such as anti-GST antibodies), or, alternatively, using agents which are enzymatically acted upon by GST to produce detectable products (e.g. 1-chloro-2,4-dinitrobenzene; Habig et al. (1974) *J Biol Chem* 249:7130). Similarly, other fusion proteins involving the p27 polypeptide and an enzymatic activity are contemplated by the present method. For example, fusion proteins containing β-galactosidase, green fluorescent protein or luciferase, to name but a few, can be employed as labels to determine the amount of p27 polypeptide sequestered on a matrix by virtue of a conjugated ubiquitin chain.

Moreover, such enzyme/p27 fusion proteins can be used to detect and quantitate ubiquitinated p27 polypeptide in a heterogeneous assay, that is one which does not require separation of the components of the conjugating system. For example, ubiquitin conjugating systems can be generated to have a ubiquitin-dependent protease which degrades the p27 fusion protein. The enzymatic activity of the fusion protein provides a detectable signal, in the presence of substrate, for measuring the level of the p27 ubiquitination. Similarly, in a non-degradative conjugating system, ubiquitination of the p27 portion of the fusion protein can allosterically influence the enzymatic activity associated with the fusion the protein and thereby provides a means for monitoring the level of ubiquitin conjugation.

In binding assay-type detection steps set out above, the choice of which of either the p27 polypeptide or ubiquitin should be specifically sequestered on the matrix will depend on a number of factors, including the relative abundance of both components in the conjugating system. For instance, where the reaction conditions of the ubiquitin conjugating system provide ubiquitin at a concentration far in excess of the level of the p27 polypeptide, (e.g., one order of magnitude or greater) sequestering the ubiquitin and detecting the amount of p27 polypeptide bound with the ubiquitin can provide less dynamic range to the detection step of the present method than the converse embodiment of sequestering the p27 polypeptide and detecting ubiquitin conjugates from the total p27 pool bound to the matrix. That is, where ubiquitin is provided in great excess relative to the p27 polypeptide, the percentage of ubiquitin conjugated p27 in the total ubiquitin bound to the matrix can be small enough that any diminishment in ubiquitination caused by an inhibitor can be made difficult to detect by the fact that, for example, the statistical error of the system (e.g. the noise) can be a significant portion of the measured change in concentration of bound p27 polypeptide. Furthermore, it is clear that manipulating the reaction conditions and reactant concentrations in the ubiquitin-conjugating system can be carried out to provide, at the detection step, greater sensitivity by ensuring that a strong ubiquitinated protein signal exists in the absence of any inhibitor.

Furthermore, drug screening assays can be generated which do not measure ubiquitination per se, but rather detect inhibitory agents on the basis of their ability to interfere with binding of the SIP polypeptides with a substrate polypeptide. In an exemplary binding assay, the compound of interest is contacted with a mixture generated from a cdc4 polypeptide and a p27 polypeptide. Detection and quantification of SIP:p27 complexes provides a means for determining the compound's efficacy at inhibiting (or potentiating) complex formation between the two polypeptides. The efficacy of the compound can be assessed by generating dose response curves from data obtained using various concentrations of the test compound. Moreover, a control assay can also be performed to provide a baseline for comparison. In the control assay, the formation of complexes is quantitated in the absence of the test compound. In certain embodiments, the binding assay can be carried out under conditions wherein ubiquitination of p27 does not occur, e.g., by the use of reaction mixtures lacking Ub or generated with ubiquitination-defective cullins protein (e.g. mutated active site) or p27 (e.g., lacking ubiquitin substrate lysine residues).

Complex formation between the SIP polypeptide and substrate polypeptides may be detected by a variety of techniques, many of which are effectively described above. For instance, modulation in the formation of complexes can be quantitated using, for example, detectably labelled proteins (e.g. radiolabelled, fluorescently labelled, or enzymatically labelled), by immunoassay, or by chromatographic detection.

Typically, it will be desirable to immobilize either one of the polypeptides to facilitate separation of complexes from uncomplexed forms of one of the proteins, as well as to accommodate automation of the assay. In an illustrative embodiment, a fusion protein can be provided which adds a domain that permits the protein to be bound to an insoluble matrix. For example, GST-SIP fusion proteins can be adsorbed onto glutathione sepharose beads (Sigma Chemical, St. Louis, Mo.) or glutathione derivatized microtitre plates, which are then combined with a p27 polypeptide, e.g. an $^{35}$S-labeled polypeptide, and the test compound and incubated under conditions conducive to complex formation. Following incubation, the beads are washed to remove any unbound p27 polypeptide, and the matrix bead-bound radiolabel determined directly (e.g. beads placed in scintillant), or in the supernatant after the complexes are dissociated, e.g. when microtitre plaste is used. Alternatively, after washing away unbound protein, the complexes can be dissociated from the matrix, separated by SDS-PAGE gel, and the level of p27 polypeptide found in the matrix-bound fraction quantitated from the gel using standard electrophoretic techniques.

In yet another embodiment, the SIP polypeptide and p27 polypeptides can be used to generate an interaction trap assay (see also, U.S. Pat. No. 5,283,317; Zervos et al. (1993) *Cell* 72:223–232; Madura et al. (1993) *J Biol Chem* 268:12046–12054; Bartel et al. (1993) *Biotechniques* 14:920–924; and Iwabuchi et al. (1993) *Oncogene* 8:1693–1696), for subsequently detecting agents which disrupt binding of the proteins to one and other.

In particular, the method makes use of chimeric genes which express hybrid proteins. To illustrate, a first hybrid gene comprises the coding sequence for a DNA-binding domain of a transcriptional activator can be fused in frame to the coding sequence for a "bait" protein, e.g., a SIP polypeptide of sufficient length to bind to p27. The second hybrid protein encodes a transcriptional activation domain fused in frame to a gene encoding a "fish" protein, e.g., a p27 polypeptide of sufficient length to interact with the SIP polypeptide portion of the bait fusion protein. If the bait and fish proteins are able to interact, e.g., form an SIP/p27 complex, they bring into close proximity the two domains of the transcriptional activator. This proximity causes transcription of a reporter gene which is operably linked to a transcriptional regulatory site responsive to the transcriptional activator, and expression of the reporter gene can be detected and used to score for the interaction of the bait and fish proteins.

In accordance with the present invention, the method includes providing a host cell, preferably a yeast cell, e.g., *Kluyverei lactis, Schizosaccharomyces pombe, Ustilaqo maydis, Saccharomyces cerevisiae, Neurospora crassa, Aspergillus niger, Aspergillus nidulans, Pichia pastoris, Candida tropicalis,* and *Hansenula polymorpha,* though most preferably *S cerevisiae* or *S. pombe*. The host cell contains a reporter gene having a binding site for the DNA-binding domain of a transcriptional activator used in the bait protein, such that the reporter gene expresses a detectable gene product when the gene is transcriptionally activated. The first chimeric gene may be present in a chromosome of the host cell, or as part of an expression vector.

The host cell also contains a first chimeric gene which is capable of being expressed in the host cell. The gene encodes a chimeric protein, e.g., the bait protein" which comprises (i) a DNA-binding domain that recognizes the responsive element on the reporter gene in the host cell, and (ii) bait protein, such as a SIP or p27 polypeptide sequence.

A second chimeric gene is also provided which is capable of being expressed in the host cell, and encodes the fish fusion protein. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid.

Preferably, the DNA-binding domain of the first hybrid protein and the transcriptional activation domain of the second hybrid protein are derived from transcriptional activators having separable DNA-binding and transcriptional activation domains. For instance, these separate DNA-binding and transcriptional activation domains are known to be found in the yeast GAL4 protein, and are known to be found in the yeast GCN4 and ADR1 proteins. Many other proteins involved in transcription also have separable binding and transcriptional activation domains which make them useful for the present invention, and include, for example, the LexA and VP16 proteins. It will be understood that other (substantially) transcriptionally-inert DNA-binding domains may be used in the subject constructs; such as domains of ACE1, λcI, lac repressor, jun or fos. In another embodiment, the DNA-binding domain and the transcriptional activation domain may be from different proteins. The use of a LexA DNA binding domain provides certain advantages. For example, in yeast, the LexA moiety contains no activation function and has no known effect on transcription of yeast genes. In addition, use of LexA allows control over the sensitivity of the assay to the level of interaction (see, for example, the Brent et al. PCT publication WO94/1 0300).

In preferred embodiments, any enzymatic activity associated with the bait or fish proteins is inactivated, e.g., dominant negative mutants of a ligase and the like can be used or mutant p27 polypeptides lacking ubiquitin-accepting lysine residues.

Continuing with the illustrated example, the SIP/p27-mediated interaction, if any, between the bait and fish fusion proteins in the host cell, therefore, causes the activation domain to activate transcription of the reporter gene. The method is carried out by introducing the first chimeric gene and the second chimeric gene into the host cell, and subjecting that cell to conditions under which the bait and fish fusion proteins and are expressed in sufficient quantity for the reporter gene to be activated. The formation of an SIP/p27 complex results in a detectable signal produced by the expression of the reporter gene. Accordingly, the formation of a complex in the presence of a test compound to the level of SIP/p27 complex in the absence of the test compound can be evaluated by detecting the level of expression of the reporter gene in each case.

In an illustrative embodiment, Saccharomyces cerevisiae YPB2 cells are transformed simultaneously with a plasmid encoding a GAL4db-SIP fusion and with a plasmid encoding the GAL4ad domain fused in-frame to a coding sequence for a p27 polypeptide. Moreover, the strain is transformed such that the GAL4-responsive promoter drives expression of a phenotypic marker. For example, the ability to grow in the absence of histidine can depend on the expression of the LacZ gene. When the LacZ gene is placed under the control of a GAL4-responsive promoter, the yeast cell will turn blue in the presence of β-gal if a functional GAL4 activator has been reconstituted through the interaction of a SIP ligase and p27. Thus, a convenient readout method is provided. Other reporter constructs will be apparent, and include, for example, reporter genes which produce such detectable signals as selected from the group consisting of an enzymatic signal, a fluorescent signal, a phosphorescent signal and drug resistance.

A similar method modifies the interaction trap system by providing a "relay gene" which is regulated by the transcriptional complex formed by the interacting bait and fish proteins. The gene product of the relay gene, in turn, regulates expression of a reporter gene, the expression of the latter being what is scored in the modified ITS assay. Fundamentally, the relay gene can be seen as a signal inverter.

As set out above, in the standard ITS, interaction of the fish and bait fusion proteins results in expression of a reporter gene. However, where inhibitors of the interaction are sought, a positive readout from the reporter gene nevertheless requires detecting inhibition (or lack of expression) of the reporter gene.

In the inverted ITS system, the fish and bait proteins positively regulate expression of the relay gene. The relay gene product is in turn a repressor of expression of the reporter gene. Inhibition of expression of the relay gene product by inhibiting the interaction of the fish and bait proteins results in concomitant relief of the inhibition of the reporter gene, e.g., the reporter gene is expressed. For example, the relay gene can be the repressor gene under control of a promoter sensitive to the SIP/p27 complex described above. The reporter gene can accordingly be a positive signal, such as providing for growth (e.g., drug selection or auxotrophic relief), and is under the control of a promoter which is constitutively active, but can be suppressed by the repressor protein. In the absence of an agent which inhibits the interaction of the fish and bait protein, the repressor protein is expressed. In turn, that protein represses expression of the reporter gene. However, an agent which disrupts binding of the SIP polypeptide and p27 proteins results in a decrease in repressor expression, and consequently an increase in expression of the reporter gene as repression is relieved. Hence, the signal is inverted.

In other embodiments, the invention provides assays, such as derived in formats set forth above, which identify agents capable of disrupting the interaction between $p19^{skp1}$, $p45^{skp2}$ or a cullins, and cdc4, e.g., such as the competitive binding assays described above.

One aspect of the present invention provides reconstituted protein preparations, e.g., purified protein combinations, including a cdc4 polypeptide plus one or more of the following proteins (or polypeptides or fusion proteins derived therefrom): an E1, an E2, p27 or other substrate protein, ubiquitin, a cullins, $p19^{skp1}$ and/or $p45^{skp2}$.

In still further embodiments of the present assay, the ubiquitin-conjugating system is generated in whole cells, taking advantage of cell culture techniques to support the subject assay. For example, as described below, the ubiquitin-conjugating system (including the p27 polypeptide and detection means) can be constituted in a eukaryotic cell culture system, including mammalian and yeast cells. Advantages to generating the subject assay in an intact cell include the ability to detect inhibitors which are functional in an environment more closely approximating that which therapeutic use of the inhibitor would require, including the ability of the agent to gain entry into the cell. Furthermore, certain of the in vivo embodiments of the assay, such as examples given below, are amenable to high through-put analysis of candidate agents.

The components of the ubiquitin-conjugating system, including the p27 polypeptide and SIP polypeptides, can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein.

In any case, the cell is ultimately manipulated after incubation with a candidate inhibitor in order to facilitate detection of ubiquitination or ubiquitin-mediated degradation of the p27 polypeptide. As described above for assays performed in reconstituted protein mixtures or lysate, the effectiveness of a candidate inhibitor can be assessed by measuring direct characteristics of the p27 polypeptide, such as shifts in molecular weight by electrophoretic means or detection in a binding assay. For these embodiments, the cell will typically be lysed at the end of incubation with the candidate agent, and the lysate manipulated in a detection step in much the same manner as might be the reconstituted protein mixture or lysate, e.g., described above.

Indirect measurement of ubiquitination of the p27 polypeptide can also be accomplished by detecting a biological activity associated with the p27 polypeptide that is either attenuated by ubiquitin-conjugation or destroyed along with the p27 polypeptide by ubiquitin-dependent proteolytic processes. As set out above, the use of fusion proteins comprising the p27 polypeptide and an enzymatic activity are representative embodiments of the subject assay in which the detection means relies on indirect measurement of ubiquitination of the p27 polypeptide by quantitating an associated enzymatic activity.

In other embodiments, the biological activity of the p27 polypeptide can be assessed by a monitoring changes in the phenotype of the targeted cell. For example, the detection means can include a reporter gene construct which includes a transcriptional regulatory element that is dependent in some form on the level of the substrate protein. For instance, the transcriptional regulatory sequence for the cyclin A gene can be used to construct the reporter gene. Expression of the cyclin A gene is dependent on cyclin E, and is inhibited by p27. In other embodiments, the substrate protein can be provided as a fusion protein with a domain which binds to a DNA element of the reporter gene construct. The added domain of the fusion protein can be one which, through its DNA-binding ability, increases or decreases transcription of the reporter gene. Which ever the case may be, its presence in the fusion protein renders it destructable by a ubiquitin-mediated pathway. Accordingly, the level of expression of the reporter gene will vary with the stability of the fusion protein.

The reporter gene product is a detectable label, such as luciferase or β-galactosidase, and is produced in the intact cell. The label can be measured in a subsequent lysate of the cell. However, the lysis step is preferably avoided, and providing a step of lysing the cell to measure the label will typically only be employed where detection of the label cannot be accomplished in whole cells.

Moreover, in the whole cell embodiments of the subject assay, the reporter gene construct can provide, upon expression, a selectable marker. A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties. For instance, the product of the reporter gene can be an enzyme which confers resistance to antibiotic or other drug, or an enzyme which complements a deficiency in the host cell (i.e. thymidine kinase or dihydrofolate reductase). To illustrate, the aminoglcycoside phosphotransferase encoded by the bacterial transposon gene Tn5 neo can be placed under transcriptional control of a promoter element responsive to the level of target p27 polypeptide present in the cell. Such embodiments of the subject assay are particularly amenable to high through-put analysis in that proliferation of the cell can provide a simple measure of inhibition of the ubiquitin-mediated degradation of the substrate polypeptide.

Other examples of reporter genes include, but are not limited to CAT (chloramphenicol acetyl transferase) (Alton and Vapnek (1979), *Nature* 282: 864–869) luciferase, and other enzyme detection systems, such as beta-galactosidase; firefly luciferase (deWet et al. (1987), *Mol. Cell. Biol.* 7:725–737); bacterial luciferase (Engebrecht and Silverman (1984), *PNAS* 1: 4154–4158; Baldwin et al. (1984), *Biochemistry* 23: 3663–3667); alkaline phosphatase (Toh et al. (1989) *Eur. J. Biochem.* 182: 231–238, Hall et al. (1983) *J. Mol. Appl. Gen.* 2: 101), human placental secreted alkaline phosphatase (Cullen and Malim (1992) *Methods in Enzymol* 216:362–368).

The amount of transcription from the reporter gene may be measured using any method known to those of skill in the art to be suitable. For example, specific mRNA expression may be detected using Northern blots or specific protein product may be identified by a characteristic stain or an intrinsic activity.

In preferred embodiments, the product of the reporter gene is detected by an intrinsic activity associated with that product. For instance, the reporter gene may encode a gene product that, by enzymatic activity, gives rise to a detection signal based on color, fluorescence, or luminescence.

The amount of expression from the reporter gene is then compared to the amount of expression in either the same cell in the absence of the test compound or it may be compared with the amount of transcription in a substantially identical cell that lacks a component of the Ub-pathway, such as an SIP ligase activity, etc.

The present invention also makes available yeast cells which contain a cdc4 null mutation. As described herein, these strains can be complemented using human genes, and thus "humanized" yeast strains can be created for in vivo drug screen, e.g., which comprise a human cdc4 homolog and (optionally) a human p27 or other substrate protein. The strain can be further manipulated to be "humanized" with respect to other biochemical steps in the SIP-mediated ubiquitination of the p27 or G1 phase cyclins (such as a D-type or E-type cyclin). For example, conditional inactivation of the relevant yeast UBC enzyme with concomitant expression of the human UBC homolog, or alternatively, replacement of other yeast genes involved in ubiquitination with their human homologs, provides a humanized system whereby the p27 protein can be ubiquitinated by a mechanism which approximates the cdc4-dependent ubiquitination that occurs in vertebrate cells.

In still another embodiment, the difference between the human SIP ligases and the yeast cdc4 can be exploited, e.g., by the use of differential screening techniques, to identify antifungal agents which have a specificity for the yeast ligase relative to the mammalian ligase. Thus, lead compounds which act specifically on pathogens, such as fungus involved in mycotic infections, can be developed. By way of illustration, any of the above assay formats, generated to compare inhibition of a fungal cdc4 with a mammalian cdc4, can be used to screen for agents which may ultimately be useful for inhibiting at least one fungus implicated in such mycosis as candidiasis, aspergillosis, mucormycosis, blastomycosis, geotrichosis, cryptococcosis, chromoblastomycosis, coccidioidomycosis, conidiosporosis, histoplasmosis, maduromycosis, rhinosporidosis, nocaidiosis, para-actinomycosis, penicilliosis, monoliasis, or sporotrichosis. For example, if the mycotic infection to which treatment is desired is candidiasis, the subject assays can comprise comparing the relative effectiveness of a test compound at inhibiting the activity of a mammalian cdc4 ligase with its effectiveness towards inhibiting the activity of a cdc4 gene cloned from yeast selected from the group consisting of *Candida albicans, Candida stellatoidea, Candida tropicalis, Candida parapsilosis, Candida krusei, Candida pseudotropicalis, Candida quillermondii*, or *Candida rugosa*. Likewise, the present assay can be used to identify anti-fungal agents which may have therapeutic value in the treatment of aspergillosis by making use of the subject assays derived from cdc4 genes cloned from yeast such as *Aspergillus fumigatus, Aspergillus flavus, Aspergillus niger, Aspergillus nidulans*, or *Aspergillus terreus*. Where the mycotic infection is mucormycosis, the cdc4 can be derived from yeast such as *Rhizopus arrhizus, Rhizopus oryzae, Absidia corymbifera, Absidia ramosa*, or *Mucor pusillus*. Sources of other yeast cdc4 ligases for comparison with a mammalian cdc4 ligase include the pathogen *Pneumocystis carinii*. Exemplary cdc4 genes from human pathogens and other lower eukaryotes are provided by, for example, GenBank Accession numbers: X96763 (*Candida albican*) and X05625 (*Saccharomyces cerevisiae*).

Exemplification

The invention now being generally described, it will be more readily understood by reference to the following examples which are included merely for purposes of illustration of certain aspects and embodiments of the present invention, and are not intended to limit the invention.

EXAMPLE 1

Cloning of a cDNA Encoding a Mouse cdc4 Protein

A full length cDNA encoding a mouse homolog of yeast cdc4 protein was cloned through its ability to specifically interact with human p19 skp1 in a yeast two hybrid system. Briefly, human skp1 was cloned into the vector pBTM116 for expression as a LexA fusion protein. This construct was transformed into S. Cerevisiae strain L40 (MATa his3 200 trp1-900 leu2-3,112 ade LYS2::lexAop)$_4$-HIS3 URA3:: (lexAop)$_8$-lacZ GAL4). Skp1 interacting clones were selected in the presence of 1 mM 3-aminotriazole after transformation of a mouse cDNA-VP16 fusion library. Specificity of the interacting clones was assessed with the D. Melanogaster daughterless gene.

Among the Skp1 interacting genes identified in this screen was 486 base pair fragment encoding a novel mouse gene which shared amino acid sequence homology with the S. Cerevisiae cdc4 gene.

EXAMPLE 2

Cloning of a Full Length cDNA Encoding a Human cdc4 Protein

This mouse cdc4 gene fragment, mcdc4, was used to clone the human homolog by low stringency hybridization from a human T cell library (Stratagene). The coding sequence for the cDNA encoding human cdc4 is shown in FIG. 1 and is set forth in SEQ ID NO: 1. This nucleic encodes a putative protein of 1121 amino acids having the amino acid sequence shown in FIG. 1 and set forth in SEQ ID NO: 2, and an apparent molecular weight of 122 kD. An alignment of the amino acid sequences of mammalian cdc4 proteins with the yeast S. cerevisae cdc4 protein indicates that the mammalian cdc4 proteins, while closely relates, share only about 15% amino acid identity with the yeast cdc4 protein.

Analysis of the mammalian clones further reveals that certain domains are conserved. In particular, a region termed the F box, and which potentially mediates the interaction of cdc4 proteins with skp1 proteins (Bai et al. (1996) Cell 86:263) is relatively well conserved among the three cdc4 proteins. The F box corresponds to a region from about amino acid 243 to about amino acid 285 of SEQ ID NO: 2. The mammalian cdc4 proteins also share significant amino acid sequence homology in a region containing six WD-40 repeats, which may serve as a platform for protein-protein interaction (Neer et al. (1994) Nature 371:297 and Sondek et al. (1996) Nature 379:369). These repeats are located from residues between approximately residues 642–1073of SEQ ID NO: 2. WD-40 repeats were initially identified in transducin's Gβ unit. Sets of 4–8 WD repeats have since been found in the sequences of about 40 other eukaryotic proteins.

EXAMPLE 3

Vertebrate cdc4 is the Functional Homolog of the Yeast cdc4 Protein

The yeast cdc4 gene is known to interact in an allele specific manner with the yeast skp1 (Bai et al., supra). Overexpression of the yeast cdc4 has been shown to rescue the skp1–11 temperature sensitive mutation but not other conditional alleles of skp1. The inactivating mutations in yeast skp1-11 were therefore engineered into human skp1 to test its interaction with the mammalian cdc4 proteins. In the two hybrid system described above, human skp1—11 was found to interact with the mouse cdc4, but not with human skp2, a previously identified interacting protein. This result suggests that the mammalian (vertebrate) cdc4 proteins (and genes) are functional homologs of the yeast cdc4.

EXAMPLE 4

Tissue Distribution of cdc4

The tissue distribution of human cdc4 was assessed by Northern analysis using a human mutiple tisse Northern blot (Clontech). With this blot, ploy A+RNA from heart, brain, placenta, lung, liver, skeletal muscle, kidney and pancreas was probed with a PCR product of the human cdc4 gene labeled by random priming. Transcripts for human cdc4 was found to be highly expressed in the pancreas, kidney and skeletal muscle and to a much lesser extent in the liver.

TABLE 2

| | cdc4 transcripts and p27 protein | |
|---|---|---|
| Tissue | cdc4 (mRNA) | p27 (protein |
| kidney | +++ | – |
| skeletal muscle | ++ | + |
| liver | + | + |
| brain | – | ++ |

Interestingly, comparing the Northern blots described above with Western blots of p27 protein published by Nakayama et al. (1996) Cell 85:707, it was observed that in certain tissues there was an inverse correlation between the expression of cdc4 and the level of p27 protein. p27 message was detected in all tissues (Polyak et al. (1994) Cell 78:59–66).

EXAMPLE 5

Cdc4 Can Form a Ubiquitin Thiolester in Vitro

Figure 2:
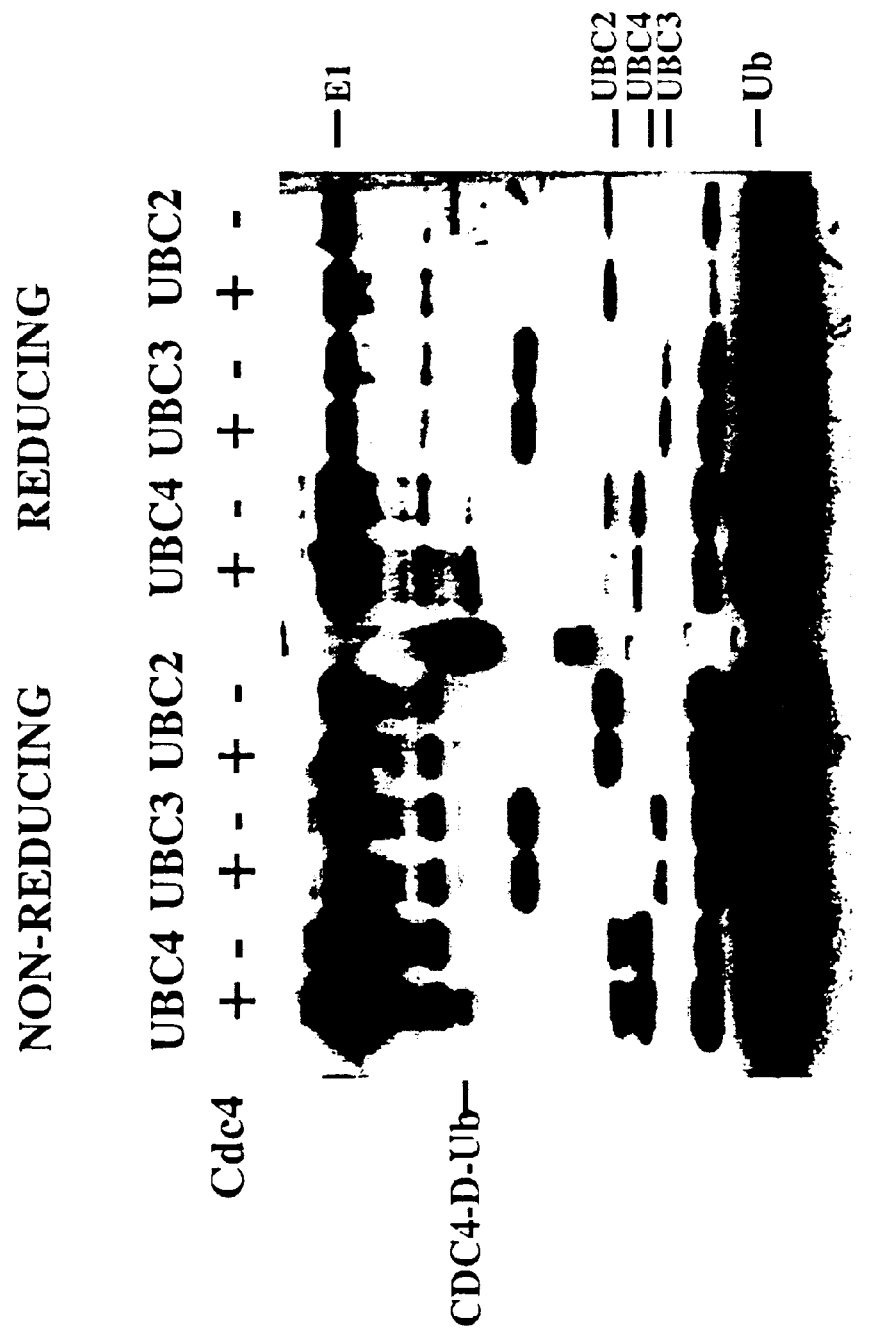

A GST-fusion protein containing amino acids 696–902 of human cdc4 was used in an in vitro ubiquitination reaction. This reaction also contained E1; one of the following E2's: UBC2, UBC3, UBC4, UBC7 or UBC-myc; and biotinylated ubiquitin for visualization of reaction products with streptavidin conjugated HRP after resolution on non-reducing SDS-PAGE. Under these reaction conditions, cdc4 polypeptide was found to be ubiquitinated by UBC4 and, though to a lesser extent, UBC2. To determine if this ubiquitin conjugation was via a thioester, the reactions were repeated except that prior to separation of the reaction products by SDS-PAGE, one half of the sample was boiled in the presence of a reducing agent. Under these conditions, the ubiquitin was removed from the cdc4 polypeptide, indicating the presence of a labile ubiquitin thiolester bond with the protein. See FIG. 2.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. An isolated nucleic acid comprising a nucleotide sequence encoding a polypeptide, or a nucleotide sequence complementary thereto, wherein said polypeptide comprises an amino acid sequence at least 95% identical to the amino acid sequence set forth in SEQ ID NO: 2, wherein said polypeptide promotes ubiquitination of a CKI (Cell-cycle dependent Kinase Inhibitor) protein.

2. The nucleic acid of claim 1, which nucleic acid hybridizes under conditions of about 1 M salt at a temperature about 20–27 C. below the melting temperature ($T_m$) of the DNA duplex formed to a nucleic acid probe having a nucleotide sequence represented by at least 60 consecutive nucleotides of SEQ ID NO: 1, or a sequence complementary thereto.

3. The nucleic acid of claim 2, which nucleic acid comprises the nucleotide sequence set forth in SEQ ID NO: 1.

4. An isolated nucleic acid comprising a nucleotide sequence encoding a polypeptide that is at least 95% identical to an amino acid sequence of SEQ ID NO: 2, wherein said polypeptide promotes ubiquitination of a G1 cyclin or a CKI (Cell-cycle dependent Kinase Inhibitor) protein.

5. The nucleic acid of claim 1, further comprising a transcriptional regulatory sequence operably linked to said nucleotide sequence so as to render said nucleic acid suitable for use as an expression vector.

6. The nucleic acid of claim 5, wherein the expression vector is capable of replicating in at least one of a prokaryotic cell and eukaryotic cell.

7. A host cell transfected with the nucleic acid of claim 6 and expressing said recombinant polypeptide.

8. A method of producing a recombinant polypeptide comprising culturing the cell of claim 7 in a cell culture medium to express said recombinant polypeptide and isolating said recombinant polypeptide from said cell culture.

9. The isolated nucleic acid of claim 1, wherein said polypeptide comprises an amino acid sequence at least 98% identical to the amino acid sequence set forth in SEQ ID NO: 2.

10. The isolated nucleic acid of claim 1, wherein said polypeptide comprises an amino acid sequence set forth in SEQ ID NO: 2.

11. An isolated nucleic acid comprising a nucleotide sequence encoding a polypeptide, or a nucleotide sequence complementary thereto, wherein said polypeptide comprises an amino acid sequence at least 95% identical to the amino acid sequence set forth in SEQ ID NO: 2, and wherein said polypeptide promotes ubiquitination of a G1 cyclin.

12. An isolated nucleic acid comprising a nucleotide sequence encoding a polypeptide, or a nucleotide sequence complementary thereto, wherein said polypeptide comprises an amino acid sequence at least 95% identical to a portion of SEQ ID NO: 2, wherein the N-terminus of said portion comprises an F box corresponding to residues 243–285 of SEQ ID NO: 2, and the C-terminus of said portion comprises a region including residues 696–902 of SEQ ID NO: 2, and said polypeptide promotes ubiquitination of a CKI protein.

13. The isolated nucleic acid of claim 1, wherein said CKI is Sic1 or p27.

14. The isolated nucleic acid of claim 1, wherein the polypeptide modulates entry of a mammalian or yeast cell into S or M phase.

15. The isolated nucleic acid of claim 1, wherein the polypeptide promotes ubiquitination of a CKI protein in the presence of at least one protein selected from: an E2 ubiquitin conjugating enzyme (UBC), a skp1, or a cullins/cdc53.

16. The isolated nucleic acid of claim 1, wherein the polypeptide comprises an F box and/or a SIP domain comprising at least residues 696–902 of SEQ ID NO: 2.

17. An isolated nucleic acid comprising the nucleotide sequence set forth in SEQ ID NO: 1, wherein the nucleic acid encodes a polypeptide that promotes ubiquitination of a CKI (Cell-cycle dependent Kinase Inhibitor) protein.

18. An isolated nucleic acid complementary to the nucleic acid of claim 17.

* * * * *

UNITED STATES PATENT AND TRADEMARK OFFICE
CERTIFICATE OF CORRECTION

PATENT NO. : 6,747,128 B2
DATED : June 8, 2004
INVENTOR(S) : Caligiuri et al.

It is certified that error appears in the above-identified patent and that said Letters Patent is hereby corrected as shown below:

<u>Column 74,</u>
Line 48, after "ubiquitination of" insert -- G1 cyclin -- and delete "CKI (Cell-cycle dependent Kinase Inhibitor)".

Signed and Sealed this

Fifth Day of April, 2005

JON W. DUDAS
*Director of the United States Patent and Trademark Office*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 3363 base pairs
      (B) TYPE: nucleic acid
      (C) STRANDEDNESS: both
      (D) TOPOLOGY: linear (ii) MOLECULE TYPE: cDNA (ix) FEATURE:
      (A) NAME/KEY: Coding Sequence
      (B) LOCATION: 1...3363
      (D) OTHER INFORMATION:

(xi) SEQUENCE DESCRIPTION: SEQ ID NO:1:

```
ATG GAC GCT CTC GAG GAC TAC GTT TGG CCG CGG GCA ACC TCG GAG CTT      48
Met Asp Ala Leu Glu Asp Tyr Val Trp Pro Arg Ala Thr Ser Glu Leu
 1               5                  10                  15

ATA CTC CTC CCA GTG ACG GGT CTG GAG TGC GTG GGG GAC CGG CTG TTG      96
Ile Leu Leu Pro Val Thr Gly Leu Glu Cys Val Gly Asp Arg Leu Leu
                20                  25                  30

GCG GGT GAG GGT CCC GAT GTC CTG GTG TAC AGC TTG GAC TTT GGT GGG     144
Ala Gly Glu Gly Pro Asp Val Leu Val Tyr Ser Leu Asp Phe Gly Gly
            35                  40                  45

CAT CTG CGG ATG ATA AAG CGA GTG CAG AAC CTG CTT GGC CAC TAT CTT     192
His Leu Arg Met Ile Lys Arg Val Gln Asn Leu Leu Gly His Tyr Leu
 50                  55                  60

ATC CAT GGC TTC CGG GTA CGG CCA GAG CCT AAT GGA GAC CTT GAC TTG     240
Ile His Gly Phe Arg Val Arg Pro Glu Pro Asn Gly Asp Leu Asp Leu
 65                  70                  75                  80

GAG GCC ATG GTG GCT GTG TTT GGA AGC AAG GGA CTC CGA GTT GTG AAA     288
Glu Ala Met Val Ala Val Phe Gly Ser Lys Gly Leu Arg Val Val Lys
                 85                  90                  95

ATT AGC TGG GGA CAG GGC CAC TTC TGG GAG CTT TGG CGC TCT GGC CTG     336
Ile Ser Trp Gly Gln Gly His Phe Trp Glu Leu Trp Arg Ser Gly Leu
            100                 105                 110

TGG AAC ATG TCT GAC TGG ATT TGG GAT GCA CGC TGG CTT GAG GGA AAT     384
Trp Asn Met Ser Asp Trp Ile Trp Asp Ala Arg Trp Leu Glu Gly Asn
        115                 120                 125

ATA GCC TTG GCC CTG GGC CAC AAC TCA GTG GTG CTA TAT GAC CCT GTA     432
Ile Ala Leu Ala Leu Gly His Asn Ser Val Val Leu Tyr Asp Pro Val
    130                 135                 140

GTA GGG TGC ATC CTG CAA GAG GTG CCC TGC ACA GAC AGG TGC ACC CTC     480
Val Gly Cys Ile Leu Gln Glu Val Pro Cys Thr Asp Arg Cys Thr Leu
145                 150                 155                 160

TCT TCA GCC TGC CTG ATT GGA GAC GCC TGG AAG GAG CTG ACC ATA GTG     528
Ser Ser Ala Cys Leu Ile Gly Asp Ala Trp Lys Glu Leu Thr Ile Val
                165                 170                 175

GCA GGT GCT GTT TCC AAC CAG CTC TTG GTC TGG TAC CCA GCA ACT GCC     576
Ala Gly Ala Val Ser Asn Gln Leu Leu Val Trp Tyr Pro Ala Thr Ala
            180                 185                 190

TTA GCA GAC AAC AAA CCT GTA GCA CCT GAC CGA CGA ATC AGT GGG CAT     624
Leu Ala Asp Asn Lys Pro Val Ala Pro Asp Arg Arg Ile Ser Gly His
        195                 200                 205

GTG GGC ATC ATC TTC AGC ATG TCA TAC CTG GAA AGC AAG GGA TTG CTG     672
Val Gly Ile Ile Phe Ser Met Ser Tyr Leu Glu Ser Lys Gly Leu Leu
```

```
                210                     215                     220
GCT ACA GCT TCA GAA GAC CGA AGC GTT CGT ATC TGG AAG GTG GGC GAC      720
Ala Thr Ala Ser Glu Asp Arg Ser Val Arg Ile Trp Lys Val Gly Asp
225                     230                     235                     240

CTG CGA GTG CCT GGG GGT CGG GTG CAA AAT ATT GGG CAC TGC TTT GGG      768
Leu Arg Val Pro Gly Gly Arg Val Gln Asn Ile Gly His Cys Phe Gly
                245                     250                     255

CAC AGC GCC CGT GTG TGG CAG GTC AAG CTT CTA GAG AAT TAC CTT ATC      816
His Ser Ala Arg Val Trp Gln Val Lys Leu Leu Glu Asn Tyr Leu Ile
            260                     265                     270

AGT GCA GGA GAG GAT TGT GTC TGC TTG GTG TGG AGC CAT GAA GGT GAG      864
Ser Ala Gly Glu Asp Cys Val Cys Leu Val Trp Ser His Glu Gly Glu
        275                     280                     285

ATC CTC CAG GCC TTT CGG GGA CAC CAG GGA CGT GGG ATC CGG GCC ATA      912
Ile Leu Gln Ala Phe Arg Gly His Gln Gly Arg Gly Ile Arg Ala Ile
    290                     295                     300

GCT GCC CAT GAG AGG CAG GCC TGG GTG ATC ACT GGG GGT GAT GAC TCA      960
Ala Ala His Glu Arg Gln Ala Trp Val Ile Thr Gly Gly Asp Asp Ser
305                     310                     315                     320

GGC ATT CGG CTG TGG CAC TTG GTA GGG CGT GGG TAC CGG GGA TTG GGG     1008
Gly Ile Arg Leu Trp His Leu Val Gly Arg Gly Tyr Arg Gly Leu Gly
                325                     330                     335

GTC TCG GCT CTC TGC TTC AAG TCC CGT AGT AGG CCA GGT ACA CTC AAG     1056
Val Ser Ala Leu Cys Phe Lys Ser Arg Ser Arg Pro Gly Thr Leu Lys
            340                     345                     350

GCT GTG ACT CTG GCT GGC TCT TGG CGA CTG CTG GCA GTG ACT GAT ACA     1104
Ala Val Thr Leu Ala Gly Ser Trp Arg Leu Leu Ala Val Thr Asp Thr
        355                     360                     365

GGG GCC CTG TAT CTC TAT GAC GTC GAG GTC AAG TGC TGG GAG CAG CTG     1152
Gly Ala Leu Tyr Leu Tyr Asp Val Glu Val Lys Cys Trp Glu Gln Leu
    370                     375                     380

CTA GAG GAT AAA CAT TTC CAG TCC TAC TGC CTG CTG GAG GCA GCT CCT     1200
Leu Glu Asp Lys His Phe Gln Ser Tyr Cys Leu Leu Glu Ala Ala Pro
385                     390                     395                     400

GGT CCC GAG GGC TTC GGA TTG TGT GCT ATG GCC AAT GGG GAA GGT CGT     1248
Gly Pro Glu Gly Phe Gly Leu Cys Ala Met Ala Asn Gly Glu Gly Arg
                405                     410                     415

GTC AAG GTT GTC CCC ATC AAC ACT CCA ACT GCT GCT GTG GAC CAG ACC     1296
Val Lys Val Val Pro Ile Asn Thr Pro Thr Ala Ala Val Asp Gln Thr
            420                     425                     430

CTG TTT CCT GGG AAG GTG CAC AGC TTG AGC TGG GCC CTG CGT GGT TAT     1344
Leu Phe Pro Gly Lys Val His Ser Leu Ser Trp Ala Leu Arg Gly Tyr
        435                     440                     445

GAG GAG CTC CTG TTG CTG GCA TCG GGC CCT GGC GGG GTA GTA GCT TGC     1392
Glu Glu Leu Leu Leu Leu Ala Ser Gly Pro Gly Gly Val Val Ala Cys
    450                     455                     460

CTA GAG ATC TCA GCC GCA CCC TCT GGC AAG GCC ATC TTT GTC AAG GAA     1440
Leu Glu Ile Ser Ala Ala Pro Ser Gly Lys Ala Ile Phe Val Lys Glu
465                     470                     475                     480

CGT TGT CGG TAC CTG CTG CCC CCA AGC AAG CAG AGA TGG CAC ACA TGC     1488
Arg Cys Arg Tyr Leu Leu Pro Pro Ser Lys Gln Arg Trp His Thr Cys
                485                     490                     495

AGT GCC TTC CTA CCC CCA GGT GAC TTC CTG GTG TGT GGT GAC CGC CGG     1536
Ser Ala Phe Leu Pro Pro Gly Asp Phe Leu Val Cys Gly Asp Arg Arg
            500                     505                     510

GGC TCT GTG CTG CTA TTC CCC TCC AGA CCA GGT CTG CTC AAG GAC CCT     1584
Gly Ser Val Leu Leu Phe Pro Ser Arg Pro Gly Leu Leu Lys Asp Pro
        515                     520                     525

GGG GTG GGA GGC AAG GCT CGG GCT GGT GCT GGG GCA CCT GTA GTG GGT     1632
```

```
                Gly Val Gly Gly Lys Ala Arg Ala Gly Ala Gly Ala Pro Val Val Gly
                                530                 535                 540

AGT GGT AGT AGT GGG GGT GGG AAT GCT TTC ACT GGG TTG GGC CCA GTC              1680
Ser Gly Ser Ser Gly Gly Gly Asn Ala Phe Thr Gly Leu Gly Pro Val
545                 550                 555                 560

TCT ACC CTG CCC TCT CTG CAC GGG AAG CAG GGT GTG ACC TCA GTC ACA              1728
Ser Thr Leu Pro Ser Leu His Gly Lys Gln Gly Val Thr Ser Val Thr
                565                 570                 575

TGC CAT GGT GGC TAT GTG TAT ACC ACA GGG CGT GAT GGA GCC TAC TAC              1776
Cys His Gly Gly Tyr Val Tyr Thr Thr Gly Arg Asp Gly Ala Tyr Tyr
            580                 585                 590

CAG CTG TTT GTA CGA GAC GGC CAG CTC CAG CCA GTC CTA AGG CAG AAG              1824
Gln Leu Phe Val Arg Asp Gly Gln Leu Gln Pro Val Leu Arg Gln Lys
        595                 600                 605

TCC TGT CGA GGC ATG AAC TGG CTA GCT GGG CTC CGT ATA GTG CCC GAT              1872
Ser Cys Arg Gly Met Asn Trp Leu Ala Gly Leu Arg Ile Val Pro Asp
610                 615                 620

GGG AGC ATG GTT ATC CTG GGT TTC CAT GCC AAT GAG TTT GTG GTG TGG              1920
Gly Ser Met Val Ile Leu Gly Phe His Ala Asn Glu Phe Val Val Trp
625                 630                 635                 640

AAC CCT CGG TCA CAC GAG AAG CTG CAC ATC GTC AAC TGT GGT GGA GGG              1968
Asn Pro Arg Ser His Glu Lys Leu His Ile Val Asn Cys Gly Gly Gly
                645                 650                 655

CAC CGT TCG TGG GCA TTC TCT GAT ACT GAG GCG GCC ATG GCC TTT GCT              2016
His Arg Ser Trp Ala Phe Ser Asp Thr Glu Ala Ala Met Ala Phe Ala
            660                 665                 670

TAC CTC AAG GAT GGG GAT GTC ATG CTG TAC AGG GCT CTG GGT GGC TGC              2064
Tyr Leu Lys Asp Gly Asp Val Met Leu Tyr Arg Ala Leu Gly Gly Cys
        675                 680                 685

ACC CGG CCA CAC GTG ATT CTC CGG GAG GGT CTG CAT GGC CGT GAG ATC              2112
Thr Arg Pro His Val Ile Leu Arg Glu Gly Leu His Gly Arg Glu Ile
690                 695                 700

ACT TGT GTA AAG CGT GTG GGC ACC ATT ACC CTG GGG CCT GAA TAT GGA              2160
Thr Cys Val Lys Arg Val Gly Thr Ile Thr Leu Gly Pro Glu Tyr Gly
705                 710                 715                 720

GTG CCC AGC TTC ATG CAG CCT GAT GAC CTG GAG CCT GGC AGT GAG GGG              2208
Val Pro Ser Phe Met Gln Pro Asp Asp Leu Glu Pro Gly Ser Glu Gly
                725                 730                 735

CCC GAC TTG ACT GAC ATT GTG ATC ACA TGT AGT GAG GAC ACT ACT GTC              2256
Pro Asp Leu Thr Asp Ile Val Ile Thr Cys Ser Glu Asp Thr Thr Val
            740                 745                 750

TGT GTC CTA GCA CTC CCT ACA ACC ACA GGC TCA GCC CAC GCA CTC ACA              2304
Cys Val Leu Ala Leu Pro Thr Thr Thr Gly Ser Ala His Ala Leu Thr
        755                 760                 765

GCT GTT TGT AAC CAT ATC TCC TCG GTA CGT GCT GTG GCT GTG TGG GGC              2352
Ala Val Cys Asn His Ile Ser Ser Val Arg Ala Val Ala Val Trp Gly
770                 775                 780

ATT GGC ACC CCA GGT GGC CCT CAG GAT CCT CAG CCA GGC CTG ACT GCC              2400
Ile Gly Thr Pro Gly Gly Pro Gln Asp Pro Gln Pro Gly Leu Thr Ala
785                 790                 795                 800

CAT GTG GTG TCT GCG GGG GGG CGG GCT GAG ATG CAC TGC TTC AGC ATC              2448
His Val Val Ser Ala Gly Gly Arg Ala Glu Met His Cys Phe Ser Ile
                805                 810                 815

ATG GTT ACT CCG GAC CCC AGC ACC CCA AGC CGC CTC GCC TGC CAT GTC              2496
Met Val Thr Pro Asp Pro Ser Thr Pro Ser Arg Leu Ala Cys His Val
            820                 825                 830

ATG CAC CTT TCG TCC CAC CGG CTA GAT GAG TAT TGG GAC CGG CAA CGC              2544
Met His Leu Ser Ser His Arg Leu Asp Glu Tyr Trp Asp Arg Gln Arg
        835                 840                 845
```

```
AAT CGG CAT CGG ATG GTT AAG GTA GAC CCA GAG ACC AGG TAC ATG TCC    2592
Asn Arg His Arg Met Val Lys Val Asp Pro Glu Thr Arg Tyr Met Ser
    850                 855                 860

CTT GCT GTG TGT GAA CTT GAC CAG CCC GGC CTT GGC CCC CTT GTG GCT    2640
Leu Ala Val Cys Glu Leu Asp Gln Pro Gly Leu Gly Pro Leu Val Ala
865                 870                 875                 880

GCA GCC TGT AGT GAT GGG GCC GTA AGG CTC TTT CTT TTG CAG GAT TCT    2688
Ala Ala Cys Ser Asp Gly Ala Val Arg Leu Phe Leu Leu Gln Asp Ser
                    885                 890                 895

GGG CGG ATT CTG CAG CTC CTT GCT GAA ACC TTC CAC CAT AAG CGA TGT    2736
Gly Arg Ile Leu Gln Leu Leu Ala Glu Thr Phe His His Lys Arg Cys
                900                 905                 910

GTC CTC AAG GTC CAC TCC TTT ACA CAC GAG GCA CCC AAC CAG AGG CGG    2784
Val Leu Lys Val His Ser Phe Thr His Glu Ala Pro Asn Gln Arg Arg
            915                 920                 925

AGG CTC CTC CTG TGC AGC GCA GCT ACT GAT GGC AGC CTG GCT TTC TGG    2832
Arg Leu Leu Leu Cys Ser Ala Ala Thr Asp Gly Ser Leu Ala Phe Trp
        930                 935                 940

GAT CTC ACC ACC ATG CTA GAC CAT GAC TCC ACT GTC CTG GAG CCT CCA    2880
Asp Leu Thr Thr Met Leu Asp His Asp Ser Thr Val Leu Glu Pro Pro
945                 950                 955                 960

GTG GAT CCT GGG CTT CCC TAC CGG CTT GGC ACC CCC TCC CTG ACT CTC    2928
Val Asp Pro Gly Leu Pro Tyr Arg Leu Gly Thr Pro Ser Leu Thr Leu
                    965                 970                 975

CAG GCC CAC AGC TGT GGT ATC AAC AGC CTG CAC ACC TTG CCC ACC CGT    2976
Gln Ala His Ser Cys Gly Ile Asn Ser Leu His Thr Leu Pro Thr Arg
                980                 985                 990

GAG GGC CAC CAT CTC GTG GCC TGT GGC AGT GAA GAT GGA TCC CTC CAT    3024
Glu Gly His His Leu Val Ala Cys Gly Ser Glu Asp Gly Ser Leu His
            995                 1000                1005

GTC TTC GTG CTT GCT GTG GAG ATG CTA CAG CTA GAA GAG GCT GTG GGA    3072
Val Phe Val Leu Ala Val Glu Met Leu Gln Leu Glu Glu Ala Val Gly
        1010                1015                1020

GAG GCT GGG CTG GTA CCC CAG CTG CGT GTG CTA GAG GAA TAC TCT GTC    3120
Glu Ala Gly Leu Val Pro Gln Leu Arg Val Leu Glu Glu Tyr Ser Val
1025                1030                1035                1040

CCC TGT GCA CAT GCT GCC CAT GTG ACA GGC CTC AAG ATC CTA AGC CCA    3168
Pro Cys Ala His Ala Ala His Val Thr Gly Leu Lys Ile Leu Ser Pro
                    1045                1050                1055

AGC ATC ATG GTC TCA GCC TCC ATT GAT CAA CGG CTG ACC TTC TGG CGT    3216
Ser Ile Met Val Ser Ala Ser Ile Asp Gln Arg Leu Thr Phe Trp Arg
                1060                1065                1070

CTG GGG CAT GGT GAA CCC ACC TTC ATG AAT AGC ACT GTG TTC CAT GTG    3264
Leu Gly His Gly Glu Pro Thr Phe Met Asn Ser Thr Val Phe His Val
            1075                1080                1085

CCT GAT GTG GCT GAC ATG GAC TGC TGG CCT GTG AGC CCT GAG TTT GGC    3312
Pro Asp Val Ala Asp Met Asp Cys Trp Pro Val Ser Pro Glu Phe Gly
        1090                1095                1100

CAC CGT TGT GCC CTT GGG GGT CAG GGG CTT GAG GTT TAC AAC TGG TAT    3360
His Arg Cys Ala Leu Gly Gly Gln Gly Leu Glu Val Tyr Asn Trp Tyr
1105                1110                1115                1120

GAT                                                                3363
Asp (2) INFORMATION FOR SEQ ID NO:2:

(i) SEQUENCE CHARACTERISTICS:
        (A) LENGTH: 1121 amino acids
        (B) TYPE: amino acid
        (C) STRANDEDNESS: single
        (D) TOPOLOGY: linear
```

(ii) MOLECULE TYPE: protein (v) FRAGMENT TYPE: internal (xi) SEQUENCE DESCRIPTION: SEQ ID NO:2:

```
Met Asp Ala Leu Glu Asp Tyr Val Trp Pro Arg Ala Thr Ser Glu Leu
 1               5                  10                  15
Ile Leu Leu Pro Val Thr Gly Leu Glu Cys Val Gly Asp Arg Leu Leu
             20                  25                  30
Ala Gly Glu Gly Pro Asp Val Leu Val Tyr Ser Leu Asp Phe Gly Gly
         35                  40                  45
His Leu Arg Met Ile Lys Arg Val Gln Asn Leu Leu Gly His Tyr Leu
     50                  55                  60
Ile His Gly Phe Arg Val Arg Pro Glu Pro Asn Gly Asp Leu Asp Leu
 65                  70                  75                  80
Glu Ala Met Val Ala Val Phe Gly Ser Lys Gly Leu Arg Val Val Lys
                 85                  90                  95
Ile Ser Trp Gly Gln Gly His Phe Trp Glu Leu Trp Arg Ser Gly Leu
            100                 105                 110
Trp Asn Met Ser Asp Trp Ile Trp Asp Ala Arg Trp Leu Glu Gly Asn
        115                 120                 125
Ile Ala Leu Ala Leu Gly His Asn Ser Val Val Leu Tyr Asp Pro Val
    130                 135                 140
Val Gly Cys Ile Leu Gln Glu Val Pro Cys Thr Asp Arg Cys Thr Leu
145                 150                 155                 160
Ser Ser Ala Cys Leu Ile Gly Asp Ala Trp Lys Glu Leu Thr Ile Val
                165                 170                 175
Ala Gly Ala Val Ser Asn Gln Leu Leu Val Trp Tyr Pro Ala Thr Ala
            180                 185                 190
Leu Ala Asp Asn Lys Pro Val Ala Pro Asp Arg Arg Ile Ser Gly His
        195                 200                 205
Val Gly Ile Ile Phe Ser Met Ser Tyr Leu Glu Ser Lys Gly Leu Leu
    210                 215                 220
Ala Thr Ala Ser Glu Asp Arg Ser Val Arg Ile Trp Lys Val Gly Asp
225                 230                 235                 240
Leu Arg Val Pro Gly Gly Arg Val Gln Asn Ile Gly His Cys Phe Gly
                245                 250                 255
His Ser Ala Arg Val Trp Gln Val Lys Leu Leu Glu Asn Tyr Leu Ile
            260                 265                 270
Ser Ala Gly Glu Asp Cys Val Cys Leu Val Trp Ser His Glu Gly Glu
        275                 280                 285
Ile Leu Gln Ala Phe Arg Gly His Gln Gly Arg Gly Ile Arg Ala Ile
    290                 295                 300
Ala Ala His Glu Arg Gln Ala Trp Val Ile Thr Gly Gly Asp Asp Ser
305                 310                 315                 320
Gly Ile Arg Leu Trp His Leu Val Gly Arg Gly Tyr Arg Gly Leu Gly
                325                 330                 335
Val Ser Ala Leu Cys Phe Lys Ser Arg Ser Arg Pro Gly Thr Leu Lys
            340                 345                 350
Ala Val Thr Leu Ala Gly Ser Trp Arg Leu Leu Ala Val Thr Asp Thr
        355                 360                 365
Gly Ala Leu Tyr Leu Tyr Asp Val Glu Val Lys Cys Trp Glu Gln Leu
    370                 375                 380
```

-continued

```
Leu Glu Asp Lys His Phe Gln Ser Tyr Cys Leu Leu Glu Ala Ala Pro
385                 390                 395                 400

Gly Pro Glu Gly Phe Gly Leu Cys Ala Met Ala Asn Gly Glu Gly Arg
            405                 410                 415

Val Lys Val Val Pro Ile Asn Thr Pro Thr Ala Ala Val Asp Gln Thr
                420                 425                 430

Leu Phe Pro Gly Lys Val His Ser Leu Ser Trp Ala Leu Arg Gly Tyr
        435                 440                 445

Glu Glu Leu Leu Leu Ala Ser Gly Pro Gly Val Val Ala Cys
450                 455                 460

Leu Glu Ile Ser Ala Ala Pro Ser Gly Lys Ala Ile Phe Val Lys Glu
465                 470                 475                 480

Arg Cys Arg Tyr Leu Leu Pro Pro Ser Lys Gln Arg Trp His Thr Cys
                485                 490                 495

Ser Ala Phe Leu Pro Pro Gly Asp Phe Leu Val Cys Gly Asp Arg Arg
            500                 505                 510

Gly Ser Val Leu Leu Phe Pro Ser Arg Pro Gly Leu Leu Lys Asp Pro
        515                 520                 525

Gly Val Gly Gly Lys Ala Arg Ala Gly Ala Gly Ala Pro Val Val Gly
        530                 535                 540

Ser Gly Ser Ser Gly Gly Gly Asn Ala Phe Thr Gly Leu Gly Pro Val
545                 550                 555                 560

Ser Thr Leu Pro Ser Leu His Gly Lys Gln Gly Val Thr Ser Val Thr
                565                 570                 575

Cys His Gly Gly Tyr Val Tyr Thr Thr Gly Arg Asp Gly Ala Tyr Tyr
            580                 585                 590

Gln Leu Phe Val Arg Asp Gly Gln Leu Gln Pro Val Leu Arg Gln Lys
        595                 600                 605

Ser Cys Arg Gly Met Asn Trp Leu Ala Gly Leu Arg Ile Val Pro Asp
        610                 615                 620

Gly Ser Met Val Ile Leu Gly Phe His Ala Asn Glu Phe Val Val Trp
625                 630                 635                 640

Asn Pro Arg Ser His Glu Lys Leu His Ile Val Asn Cys Gly Gly Gly
                645                 650                 655

His Arg Ser Trp Ala Phe Ser Asp Thr Glu Ala Ala Met Ala Phe Ala
            660                 665                 670

Tyr Leu Lys Asp Gly Asp Val Met Leu Tyr Arg Ala Leu Gly Gly Cys
        675                 680                 685

Thr Arg Pro His Val Ile Leu Arg Glu Gly Leu His Gly Arg Glu Ile
        690                 695                 700

Thr Cys Val Lys Arg Val Gly Thr Ile Thr Leu Gly Pro Glu Tyr Gly
705                 710                 715                 720

Val Pro Ser Phe Met Gln Pro Asp Asp Leu Glu Pro Gly Ser Glu Gly
                725                 730                 735

Pro Asp Leu Thr Asp Ile Val Ile Thr Cys Ser Glu Asp Thr Thr Val
            740                 745                 750

Cys Val Leu Ala Leu Pro Thr Thr Thr Gly Ser Ala His Ala Leu Thr
        755                 760                 765

Ala Val Cys Asn His Ile Ser Ser Val Arg Ala Val Ala Val Trp Gly
        770                 775                 780

Ile Gly Thr Pro Gly Gly Pro Gln Asp Pro Gln Pro Gly Leu Thr Ala
785                 790                 795                 800

His Val Val Ser Ala Gly Gly Arg Ala Glu Met His Cys Phe Ser Ile
```

```
                         805                 810                 815
Met Val Thr Pro Asp Pro Ser Thr Pro Ser Arg Leu Ala Cys His Val
            820                 825                 830

Met His Leu Ser Ser His Arg Leu Asp Glu Tyr Trp Asp Arg Gln Arg
            835                 840                 845

Asn Arg His Arg Met Val Lys Val Asp Pro Glu Thr Arg Tyr Met Ser
850                 855                 860

Leu Ala Val Cys Glu Leu Asp Gln Pro Gly Leu Gly Pro Leu Val Ala
865                 870                 875                 880

Ala Ala Cys Ser Asp Gly Ala Val Arg Leu Phe Leu Gln Asp Ser
            885                 890                 895

Gly Arg Ile Leu Gln Leu Leu Ala Glu Thr Phe His His Lys Arg Cys
            900                 905                 910

Val Leu Lys Val His Ser Phe Thr His Glu Ala Pro Asn Gln Arg Arg
            915                 920                 925

Arg Leu Leu Leu Cys Ser Ala Ala Thr Asp Gly Ser Leu Ala Phe Trp
930                 935                 940

Asp Leu Thr Thr Met Leu Asp His Asp Ser Thr Val Leu Glu Pro Pro
945                 950                 955                 960

Val Asp Pro Gly Leu Pro Tyr Arg Leu Gly Thr Pro Ser Leu Thr Leu
            965                 970                 975

Gln Ala His Ser Cys Gly Ile Asn Ser Leu His Thr Leu Pro Thr Arg
            980                 985                 990

Glu Gly His His Leu Val Ala Cys Gly Ser Glu Asp Gly Ser Leu His
            995                 1000                1005

Val Phe Val Leu Ala Val Glu Met Leu Gln Leu Glu Glu Ala Val Gly
            1010                1015                1020

Glu Ala Gly Leu Val Pro Gln Leu Arg Val Leu Glu Glu Tyr Ser Val
1025                1030                1035                1040

Pro Cys Ala His Ala Ala His Val Thr Gly Leu Lys Ile Leu Ser Pro
                    1045                1050                1055

Ser Ile Met Val Ser Ala Ser Ile Asp Gln Arg Leu Thr Phe Trp Arg
            1060                1065                1070

Leu Gly His Gly Glu Pro Thr Phe Met Asn Ser Thr Val Phe His Val
            1075                1080                1085

Pro Asp Val Ala Asp Met Asp Cys Trp Pro Val Ser Pro Glu Phe Gly
            1090                1095                1100

His Arg Cys Ala Leu Gly Gly Gln Gly Leu Glu Val Tyr Asn Trp Tyr
1105                1110                1115                1120

Asp (2) INFORMATION FOR SEQ ID NO:3:

(i) SEQUENCE CHARACTERISTICS:
        (A) LENGTH: 484 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: Coding Sequence
        (B) LOCATION: 1...484
        (D) OTHER INFORMATION:

(xi) SEQUENCE DESCRIPTION: SEQ ID NO:3:
```

```
ACC TTC ACA CAT GAG GCA CCT AAC CAG CGT CGG AGG CTG ATC CTG TGC      48
Thr Phe Thr His Glu Ala Pro Asn Gln Arg Arg Arg Leu Ile Leu Cys
 1               5                  10                  15

AGT GCA GCT ACA GAT GGC AGC CTA GCC TTC TGG GAT CTC ACC ACG GCA      96
Ser Ala Ala Thr Asp Gly Ser Leu Ala Phe Trp Asp Leu Thr Thr Ala
                 20                  25                  30

ATG GAC AAA GGC TCT ACT ACC CTG GAG CTT CCA GCA CAC CCT GGG CTT     144
Met Asp Lys Gly Ser Thr Thr Leu Glu Leu Pro Ala His Pro Gly Leu
             35                  40                  45

CCC TAC CAG ATG GGC ACC CCC TCC ATG ACC GTG CAA GCC CAT AGC TGT     192
Pro Tyr Gln Met Gly Thr Pro Ser Met Thr Val Gln Ala His Ser Cys
         50                  55                  60

GGC GTC AAT AGC CTG CAC ACT TTG CCT ACA CCT GAG GGC CAC CAC CTT     240
Gly Val Asn Ser Leu His Thr Leu Pro Thr Pro Glu Gly His His Leu
 65                  70                  75                  80

GTG GCC AGT GGC AGT GAG GAT GGG TCC CTG CAT GTC TTC ACA CTT GCT     288
Val Ala Ser Gly Ser Glu Asp Gly Ser Leu His Val Phe Thr Leu Ala
                     85                  90                  95

GTG AAG ATG CCA GAG CCG GAA GAA GCT GAT GGG GAG GCT GAG CTG GTG     336
Val Lys Met Pro Glu Pro Glu Glu Ala Asp Gly Glu Ala Glu Leu Val
                100                 105                 110

CCC CAG TTA TGT GTC CTA GAG GAA TAT TCC GTC CCC TGC GCA CAT GCT     384
Pro Gln Leu Cys Val Leu Glu Glu Tyr Ser Val Pro Cys Ala His Ala
            115                 120                 125

GCC CAT GTG ACA GGC GTC AAG ATC CTA AGT CCC AAG CTC ATG GTC TCA     432
Ala His Val Thr Gly Val Lys Ile Leu Ser Pro Lys Leu Met Val Ser
        130                 135                 140

GCC TCC ATA GAC CAG CGG CTG ACC TTC TGG CGT CTG GGA CAG GGT GAG     480
Ala Ser Ile Asp Gln Arg Leu Thr Phe Trp Arg Leu Gly Gln Gly Glu
145                 150                 155                 160

CCC A                                                                484
Pro Pro (2) INFORMATION FOR SEQ ID NO:4:

(i) SEQUENCE CHARACTERISTICS:
        (A) LENGTH: 162 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

Thr Phe Thr His Glu Ala Pro Asn Gln Arg Arg Arg Leu Ile Leu Cys
 1               5                  10                  15

Ser Ala Ala Thr Asp Gly Ser Leu Ala Phe Trp Asp Leu Thr Thr Ala
                 20                  25                  30

Met Asp Lys Gly Ser Thr Thr Leu Glu Leu Pro Ala His Pro Gly Leu
             35                  40                  45

Pro Tyr Gln Met Gly Thr Pro Ser Met Thr Val Gln Ala His Ser Cys
         50                  55                  60

Gly Val Asn Ser Leu His Thr Leu Pro Thr Pro Glu Gly His His Leu
 65                  70                  75                  80

Val Ala Ser Gly Ser Glu Asp Gly Ser Leu His Val Phe Thr Leu Ala
                     85                  90                  95

Val Lys Met Pro Glu Pro Glu Glu Ala Asp Gly Glu Ala Glu Leu Val
                100                 105                 110
```

```
                    -continued
Pro Gln Leu Cys Val Leu Glu Glu Tyr Ser Val Pro Cys Ala His Ala
        115                 120                 125

Ala His Val Thr Gly Val Lys Ile Leu Ser Pro Lys Leu Met Val Ser
    130                 135                 140

Ala Ser Ile Asp Gln Arg Leu Thr Phe Trp Arg Leu Gly Gln Gly Glu
145                 150                 155                 160

Pro Pro
```